US010515256B2

(12) United States Patent
McLeod et al.

(10) Patent No.: US 10,515,256 B2
(45) Date of Patent: Dec. 24, 2019

(54) CELLULOSE ACETATE TOW BANDS AND FILTERS WITH SURFACE MARKINGS

(71) Applicant: Eastman Chemical Company, Kingsport, TN (US)

(72) Inventors: Andrew Ervin McLeod, Jonesborough, TN (US); Kevin Todd Barham, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 16/114,383

(22) Filed: Aug. 28, 2018

(65) Prior Publication Data
US 2019/0080147 A1    Mar. 14, 2019

Related U.S. Application Data

(60) Provisional application No. 62/557,248, filed on Sep. 12, 2017.

(51) Int. Cl.
| | |
|---|---|
| *G06K 19/06* | (2006.01) |
| *G06K 9/00* | (2006.01) |
| *A24D 3/06* | (2006.01) |
| *A24D 3/10* | (2006.01) |
| *D06P 5/30* | (2006.01) |
| *C08L 1/12* | (2006.01) |
| *D06M 10/00* | (2006.01) |
| *D06M 23/16* | (2006.01) |
| *G01N 33/36* | (2006.01) |
| *G01N 21/84* | (2006.01) |
| *G06K 7/10* | (2006.01) |
| *G06K 7/14* | (2006.01) |
| *D06M 101/08* | (2006.01) |
| *D06H 1/00* | (2006.01) |
| *A24D 3/04* | (2006.01) |
| *D01F 2/28* | (2006.01) |

(52) U.S. Cl.
CPC ......... *G06K 9/00147* (2013.01); *A24D 3/063* (2013.01); *A24D 3/10* (2013.01); *C08L 1/12* (2013.01); *D06M 10/005* (2013.01); *D06M 23/16* (2013.01); *D06P 5/30* (2013.01); *G06K 19/06028* (2013.01); *G06K 19/06046* (2013.01); *A24D 3/04* (2013.01); *D01F 2/28* (2013.01); *D06H 1/00* (2013.01); *D06M 2101/08* (2013.01); *G01N 33/365* (2013.01); *G01N 2021/8444* (2013.01); *G06K 7/1413* (2013.01); *G06K 7/1417* (2013.01); *G06K 2007/10504* (2013.01); *G06K 2009/0059* (2013.01)

(58) Field of Classification Search
None
See application file for complete search history.

(56) References Cited

U.S. PATENT DOCUMENTS

| | | | |
|---|---|---|---|
| 951,147 A | 3/1910 | Porter | |
| 4,280,925 A | 7/1981 | Kiefer | |
| 4,390,452 A | 6/1983 | Stevens | |
| 4,838,642 A | 6/1989 | De Jong et al. | |
| 5,744,000 A | 4/1998 | Athey et al. | |
| 6,607,813 B2 | 8/2003 | Washburn et al. | |
| 6,948,068 B2 | 9/2005 | Lawandy et al. | |
| 7,162,286 B2 | 1/2007 | Knoll et al. | |
| 7,163,744 B2 | 1/2007 | Nightingale et al. | |
| RE39,490 E | 2/2007 | Cote et al. | |
| 7,546,048 B2 | 6/2009 | Schwartz et al. | |
| 7,684,652 B2 | 3/2010 | Zorab et al. | |
| 7,995,196 B1 | 8/2011 | Fraser | |
| 8,158,253 B2 | 4/2012 | Spinks | |
| 8,171,567 B1 | 5/2012 | Fraser et al. | |
| 8,409,705 B2 | 4/2013 | Spinks | |
| 8,748,079 B2 | 6/2014 | True | |
| 8,851,384 B2 | 10/2014 | Iwamoto | |
| 8,862,264 B2 | 10/2014 | Phan et al. | |
| 8,900,414 B2 | 12/2014 | Käser | |
| 9,320,994 B2 * | 4/2016 | McLeod | G07D 7/2033 |
| 9,442,074 B2 * | 9/2016 | McLeod | G01N 21/84 |
| 9,851,341 B2 | 12/2017 | Gaynor et al. | |
| 9,863,920 B2 | 1/2018 | Gaynor et al. | |
| 9,865,182 B2 | 1/2018 | McLeod et al. | |
| 9,916,482 B2 | 3/2018 | McLeod et al. | |
| 9,972,224 B2 | 5/2018 | Renfro et al. | |
| 2001/0037455 A1 | 11/2001 | Lawandy et al. | |
| 2002/0067603 A1 | 6/2002 | Driscoll et al. | |
| 2003/0006324 A1 | 1/2003 | Pettigrew et al. | |
| 2003/0058990 A1 | 3/2003 | Kaiser et al. | |
| 2004/0034214 A1 | 2/2004 | Nightingale et al. | |
| 2005/0227068 A1 | 10/2005 | Dugan | |
| 2007/0098974 A1 | 5/2007 | Nightingale et al. | |
| 2007/0161115 A1 | 7/2007 | Schwartz et al. | |
| 2008/0019924 A1 | 1/2008 | Kittler, Jr. et al. | |
| 2008/0216255 A1 | 9/2008 | Poovey et al. | |
| 2010/0239642 A1 | 9/2010 | Campbell et al. | |
| 2015/0376818 A1 * | 12/2015 | McLeod | G07D 7/2033 19/66 T |
| 2015/0376819 A1 | 12/2015 | McLeod et al. | |
| 2015/0377792 A1 | 12/2015 | Renfro et al. | |
| 2015/0377841 A1 * | 12/2015 | Gaynor | A24D 3/04 436/154 |
| 2015/0379703 A1 * | 12/2015 | McLeod | G07D 7/2033 382/152 |
| 2015/0379903 A1 * | 12/2015 | McLeod | G01N 21/84 235/454 |
| 2018/0144161 A1 * | 5/2018 | McLeod | G01N 21/84 |

FOREIGN PATENT DOCUMENTS

| | | | |
|---|---|---|---|
| CN | 202298350 U | 7/2012 | |
| JP | 2000 314045 A | 11/2000 | |

(Continued)

OTHER PUBLICATIONS http://www.gtin.info/barcode-101.

(Continued)

*Primary Examiner* — Christle I Marshall
(74) *Attorney, Agent, or Firm* — Dennis V. Carmen

(57) ABSTRACT

Disclosed are acetate tow bands comprising identification fibers made of cellulose acetate which exhibit surface markings in a repeated pattern along the length of the identification fibers. The identification fibers can be incorporated into an acetate tow band. The surface markings and repeated pattern can be representative of a bale identifier. The identification fibers can be recovered from a cigarette filter, the repeated pattern decoded, and supply chain information associated with the acetate tow band used to make the cigarette filter can be obtained.

20 Claims, 12 Drawing Sheets

(56) References Cited

FOREIGN PATENT DOCUMENTS

| RU | 2 080 428 C1 | 5/1997 |
|---|---|---|
| WO | WO 95/09947 A1 | 4/1995 |
| WO | WO 99/63145 A1 | 12/1999 |
| WO | WO 2011/073442 A1 | 6/2011 |
| WO | WO 2013/089688 A1 | 6/2013 |
| WO | WO 2016/179220 A1 | 11/2016 |

OTHER PUBLICATIONS

Huang, Chaobo, et al.; "Digitally Encoded Nanoscopic Polymeric Fibers Prepared by Electrospinning"; Polymer Preprints, vol. 50, Issue 1; p. 92; 2009.

Huang, C. et al.; "Unbreakable Codes in Electrospun Fibers: Digitally Encoded Polymers to Stop Medicine Counterfeiting"; Advanced Materials, vol. 22, Issue 24; pp. 2657-2668; May 5, 2010.

McBride, Murdoch; "Tobacco's Illicit Trade—How Legislation, Enforcement and Public Awareness Are Key to Tackling Illicit Trade, Part I—Overview"; Tobacco International; pp. 17-27; Dec. 2013.

Notification of Transmittal of the International Search Report and the Written Opinion of the International Searching Authority, or the Declaration dated Sep. 30, 2015 received in International Application No. PCT/US2015/037637.

Notification of Transmittal of the International Search Report and the Written Opinion of the International Searching Authority, or the Declaration dated Nov. 30, 2018 received in International Application No. PCT/US2018/049692.

\* cited by examiner

Schematic of concurrent surface marking and acetate tow production

An image of a 20 dpf monofilament cellulose ester fiber engraved using a MACSA carbon dioxide laser Schematic of experimental laser etching process Coding on 20 dpf Cellulose Acetate Fiber of Example 3

Coding on 20 dpf Cellulose Acetate Fiber of Example 3

CELLULOSE ACETATE TOW BANDS AND FILTERS WITH SURFACE MARKINGS

CROSS REFERENCES TO RELATED APPLICATIONS

This application claims priority under 35 U.S.C. 119(e) to U.S. Provisional Application Ser. No. 62/557,248, filed Sep. 12, 2017, the contents of which is incorporated herein by reference in its entirety.

TECHNICAL FIELD

The present disclosure relates to acetate tow bands and filters made from acetate tow bands comprising identification fibers comprising cellulose acetate. The identification fibers have a larger denier per filament than the standard fibers and exhibit a repeated pattern of surface markings. The repeated pattern of surface markings can correlate to supply chain information of the acetate tow band and/or filter. The present disclosure also relates to the method for making and characterizing the acetate tow band containing the identification fibers. Characterizing of the acetate tow band and/or filter can include isolating the identification fibers, decoding the repeated pattern of surface markings, and correlating the repeated pattern of surface markings to supply chain information.

BACKGROUND

Many industries have a need to mark, tag, or identify products that allows for the tracking and tracing of products through the supply chain. One of the primary purposes for such track and trace systems is the combating of illicit trade such as counterfeiting and black market sales.

Anti-counterfeiting measures (ACMs) can be regarded as three different types: Type I (Overt), Type II (Covert) and Type III (Forensic). Type I ACMs are features incorporated into an article that are readily identified and observable to the naked eye. Examples include watermarks, color shifting inks, colored fibers, bands, or strips incorporated into the article, and holograms. Type II ACMs are features that are incorporated into the article that require some form of instrument to identify the feature in the field. The instruments required are generally those that are readily available and transportable. Some examples include the incorporation of very small text (requiring the use of a magnifying glass), UV responsive inks or threads (requiring illumination with a UV light), and barcodes or RFID tags (requiring a specialized reader). Type III ACMs are hidden attributes that require specialized laboratory equipment to identify. Some Type III examples include nano-text, micro-taggants, DNA inks, and chemical additives.

As stated above, there are many widely-used packaging and labelling taggants and anti-counterfeiting measures (ACMs) in many industries, but these more overt solutions are often susceptible to countermeasures such as destruction, modification, duplication, repackaging, or relabeling. Altering the physical features of the raw materials of a product can provide a more covert solution that is much more difficult to evade. These taggants may be used to track an acetate tow band through the supply chain. The taggants may change the physical properties of some fibers, yarn fiber bands, and/or derivative articles in a manner that is difficult to copy or alter but is detectable using image analysis and/or other mechanical methods.

The disclosed exemplary embodiments can be used, for example, to combat the continuing and growing illicit-trade problem of tobacco products, particularly cigarettes. It has been estimated that 10-12% of all cigarette sales are illicit, either counterfeit copies or sales that avoid paying excise taxes on the cigarettes (Tobacco International, "Tackling Illicit Trade, Pt. I," December 2013). To combat this illicit trade requires a global effort consisting of manufacturers, distributors, regulators, and customs/law enforcement, as well as retailers who sell the cigarettes to consumers. There is a need to be able to track and ultimately trace components used in the construction of a cigarette. For example, the ability to track part of the supply chain path of acetate tow contained in the filter of a black-market cigarette may give helpful information on the source of these illicit cigarettes.

Identification tags can be incorporated into the acetate tow band and can denote, for example, manufacturer, manufacture site, customer, and ship-to location among other supply chain information that might be useful for the track and trace of the acetate tow bands, filter rods, and/or cigarette filters.

Manufacturers of acetate tow typically assign a bale identifier (e.g., number) to each bale of acetate tow produced. Upon assignment, the bale number is associated with supply chain components such as manufacturer, manufacturing site, manufacturing line, production run, and production date. As the bale of acetate tow moves through the supply chain, additional supply chain components such as, for example, customer and ship-to location can be associated with the bale number. In other words, acetate tow manufacturers have systems in place to track and trace some of the supply chain components for bales of acetate tow. Currently, however, an equivalent of a bale number is not encoded in the acetate tow band itself. Therefore, once the label is removed from a bale of acetate tow or the acetate tow band is converted into a filter rod or cigarette filter, the supply chain information is lost.

There is a need for a traceable acetate tow band that is readily manufactured, does not impact the performance of a cigarette filter, and is detectable, not only in an acetate tow band, but also in a single or a set of cigarettes/cigarette filters. There is a need for a traceable acetate tow band that is readily accepted by cigarette manufacturers and consumers, such as an acetate tow that does not require adding chemicals which may impact sensory perception. There is a need for a traceable acetate tow band that does not impact the pressure drop and yield of a cigarette filter. There is a need for a traceable acetate tow band that maintains its traceability when bloomed, plasticized, formed into a filter, and throughout the product cycle of the filter being incorporated into a cigarette and the cigarette reaching the consumer.

There is a need for traceable acetate tow that contains supply chain information including a manufacturer, the customer, or the ship-to location such that the information can be decoded from a single or a set of cigarettes. There is a further need for traceable acetate tow with supply chain information at the level of the acetate tow bale in order to implement a traceable acetate tow system with minimal supply chain costs and complexities.

BRIEF SUMMARY

In one embodiment, an acetate tow band comprises fibers. The fibers comprise identification fibers and standard fibers. The standard fibers and identification fibers comprise cellulose acetate. A ratio of a size of the identification fibers to a size of the standard fibers ($dpf_{ID\ fibers}$:$dpf_{STD\ fibers}$) is 1.5:1 or greater. The identification fibers exhibit one or more taggant surface markings. The taggant surface markings form a repeated pattern along a length of the identification fibers. The taggant surface markings and the repeated pattern are representative of a bale identifier of the acetate tow band.

In another embodiment, a method of making an acetate tow band comprises: (a) obtaining the identification fibers; (b) producing the standard fibers on a first fiber production process; and (c) combining the identification fibers and the standard fibers into the acetate tow band. The fibers comprise standard fibers and identification fibers. The standard fibers and identification fibers comprise cellulose acetate. A ratio of a size of the identification fibers to a size of the standard fibers ($dpf_{ID\ fibers}$:$dpf_{STD\ fibers}$) is 1.5:1 or greater. The identification fibers exhibit one or more taggant surface markings. The taggant surface markings form a repeated pattern along a length of the identification fibers. The taggant surface markings and the repeated pattern are representative of a bale identifier of the acetate tow band.

In yet another embodiment a method of characterizing a cigarette filter is disclosed. The cigarette filter comprises an acetate tow band and the acetate tow band comprises fibers. The fibers comprise standard fibers and identification fibers. The standard fibers and identification fibers comprise cellulose acetate. A ratio of a size of the identification fibers to a size of the standard fibers ($dpf_{ID\ fibers}$:$dpf_{STD\ fibers}$) is 1.5:1 or greater. The identification fibers exhibit one or more taggant surface markings. The taggant surface markings form a repeated pattern along a length of the identification fibers. The method comprises (a) locating the identification fibers by exploiting the ratio of the size of the identification fibers to the size of the standard fibers; (b) separating the identification fibers from the cigarette filter; (c) applying imaging technology to at least one of the identification fibers; (d) detecting the taggant surface markings; (e) determining the repeated pattern of the taggant surface markings, wherein the taggant surface markings and the repeated pattern are representative of at least one supply chain component of the acetate tow band; and (f) generating, based on the detection and determination, supply chain information correlating the taggant surface markings and the repeated pattern to at least one supply chain component of the acetate tow band.

DETAILED DESCRIPTION

Figure 1:
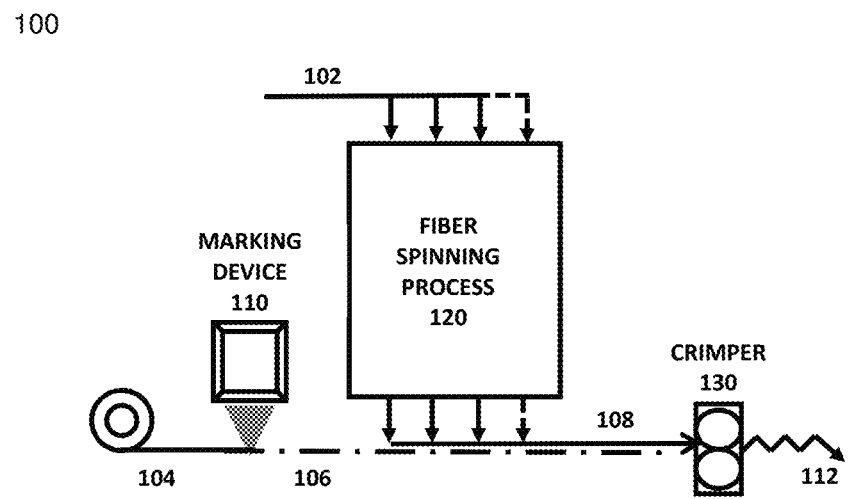
FIG. 1 shows a schematic process flow diagram of a non-limiting embodiment of applying surface markings to cellulose acetate fibers while coproducing acetate tow fibers and combining them into an acetate tow band.

In one embodiment, an acetate tow band comprises fibers. The fibers comprise identification fibers and standard fibers. The standard fibers and identification fibers comprise cellulose acetate. A ratio of a size of the identification fibers to a size of the standard fibers ($dpf_{ID\ fibers}$:$dpf_{STD\ fibers}$) is 1.5:1 or greater. The identification fibers exhibit one or more taggant surface markings. The taggant surface markings form a repeated pattern along a length of the identification fibers. The taggant surface markings and the repeated pattern are representative of a bale identifier of the acetate tow band.

Unless otherwise indicated, all numbers expressing quantities of ingredients, properties such as molecular weight, reaction conditions, and so forth used in the specification and claims are to be understood as being modified in all instances by the term "about."

It is to be understood that the mention of one or more process steps does not preclude the presence of additional process steps before or after the combined recited steps or intervening process steps between those steps expressly identified. Moreover, the lettering of process steps is a convenient means for identifying discrete activities and the recited lettering can be arranged in any sequence, unless otherwise indicated.

As used herein the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The term "fibers", as used herein, refers to thin flexible threadlike objects. The term "filament", as used herein, refers to a single fiber.

Fibers can be identification fibers and/or standard fibers. The term "standard fibers", as used herein, refers to fibers which are manufactured for the primary purpose and use in producing articles. Standard fibers have not been purposefully manipulated to comprise distinct features used to identify and track the acetate tow band or a filter comprising the acetate tow band. The term "identification fibers", as used herein, refers to the fibers having distinct features such that the identification fibers can be used to identify and track the acetate tow band and/or a filter comprising the acetate tow band.

The term "distinct features", as used herein, refers to variances among fibers that can be identified using imaging technology. Non-limiting examples of distinct features include cross-section shapes, cross-section sizes, optical properties, and surface markings.

The term, "surface markings", as used herein, refers to variances in the fibers produced by physically altering the fiber surface. Non-limiting examples include engraving the fiber, morphological modification, and printing on the fiber surface. The term "taggant surface markings", as used herein refers to a collection of known surface markings used by one or more manufacturer in a system for determining supply chain information.

The term "alphanumeric code", as used herein, refers to information that is represented using the characters or letterings belonging to a common alphabetic and numerical system or language, including special characters such as punctuation marks and including any script or printing style for that language. Non-limiting examples include the Latin alphabet, Roman numerals, and Arabic numbering.

The term "digital code", as used herein, refers to information that is represented using a string of discrete, discontinuous values. Non-limiting examples include binary coding systems, Morse Code, bar coding systems (including 1-D linear and 2-D matrix), The term "analog code", as used herein, refers to information that is represented by modulating a continuously variable physical quantity such as spatial position, a dimension, or a magnitude.

The term an "ideographic code", as used herein, refers to information that is represented by a graphic symbol or pictograph, independent of any particular language or alphanumeric system.

The term "metadata", as used herein, refers to a portion or multiple portions of the pattern that represents a code that contains information about the remaining code within the pattern. Non-limiting examples of this information includes the format, read-start position, read-end position, read direction of any code the pattern represents. The metadata could also include information that represents the manufacturer of the acetate tow band. The metadata may use the same or similar coding system as that used for the remaining portion of the pattern or it may use a different coding system to easily differentiate it from the remaining portion of the pattern.

The term "read-start position," as used herein, refers to the position where a code or a portion of a code begins.

The term "read-end position," as used herein, refers to the position where a code or a portion of a code ends.

The term "read-direction," as used herein, refers to the linear direction a particular portion of the code must be read to reliably decode the information.

The term "the repeated pattern is essentially one-dimensional", as used herein, refers to a pattern where the useful information associated with the pattern is along one direction or can be determined by observing the variation along a single line through the pattern.

The term "engraving", as used herein, refers to the removal of material from the fiber surface or the creation of raised or recessed areas on the fiber surface such that the resulting discontinuities in the fiber surface can be detected optically or by other analytical means. Engraving can be performed by contact equipment, such as equipment that uses abrasive surfaces, blades, or embossers, or by noncontact equipment, such as lasers or other high energy radiation sources. The resulting discontinuities in the fiber surface for "laser engraving" or other engraving mechanisms applied to cellulose acetate fibers may be detected optically by the corresponding surface color markings.

The term "laser engraving", as used herein, refers the use of a laser to engrave the surface of a fiber.

The term "vary along the length", as used herein, refers to the use of various levels and/or patterns of one or more surface markings along the length of an identification fiber.

The term, "repeating patterns", as used herein, refers to a repeated identical sequence of surface makings along the length of the identification fibers. Each repeated pattern is representative of the same code of the same information.

The term, "cellulose acetate", as used herein, refers to an acetate ester of cellulose wherein the hydrogen in the hydroxyl groups of the cellulose glucose unit is replaced by acetyl groups through an acetylation reaction. In some embodiments, suitable cellulose acetates may have a degree of substitution less than about 3 acetyl groups per glucose unit, preferably in the range of 2.2 to about 2.8, and most preferably in the range of 2.4 to 2.7.

The terms, "cellulose acetate tow", "acetate tow", or "acetate tow band" as used herein, refers to a continuous, crimped fiber band comprising cellulose acetate fibers.

The term, "filter", as used herein refers to a semi-permeable fibrous material. Non-limiting examples of filters include a filter rod, and items made from a filter rod such as a cigarette filter. The term "filter rod", as used herein, refers to a rod-like article, of any cross-sectional shape, produced from an acetate tow band and other components or additives, which can be subsequently used as a whole unit, or cut into lengths to form multiple units, for filtration of a vapor stream. Filter rods can be used to filter tobacco products, for example, traditional cigarette filters and/or other applications for other tobacco products including heat-not-burn products. Filter rods can also be used for new products comprising tobacco and other ingredients such as, for example, other plants or plant derivatives. Filter rods can be used to filter other plants and plant derivatives, with or without tobacco present. Additionally, filter rods can be used to filter any vapor stream used to deliver an active ingredient such as in e-cigarette.

The term, "cigarette filter", as used herein, refers to a component of the cigarette or other smoking device which removes or decreases one or more elements from a smoke stream. The term cigarette filter is intended to encompass the filter on any smoking device including the non-limiting examples of a cigarette, a cigarette holder, a cigar, a cigar holder, a pipe, a water pipe, a hookah, an electronic smoking device, a roll-your-own cigarette, a roll-your-own cigar, and a paper.

The term, "supply chain information" as used herein, refers to information regarding the production of the acetate two band and information regarding the distribution of the acetate tow band. Supply chain information includes "supply chain components" such as, for example, manufacturer, manufacture site, manufacture line, production run, production date, a package, bale, customer, customer ship-to location, warehouses, freight carrier, and/or shipment paths or routes.

The term, "manufacturer", as used herein, refers to the entity that produces the acetate tow band.

The term "manufacture site", as used herein, refers to the geographic location or locations of the manufacturer, designated by any level of specificity including full address, continent, country, state, province, county, or city.

The term "manufacture line", as used herein, refers to specific process equipment or set of equipment used by the manufacturer to produce the acetate tow band.

The term "production run", as used herein, refers to a group or set of similar or related goods that are produced by using a particular set of manufacturing procedures, processes, or conditions and/or product specifications.

The term "customer", as used herein, refers to an entity to which the acetate tow band is sold and shipped for further processing into a filter rod or a cigarette; or an entity that purchases the acetate tow band for resale.

The term, "ship-to location", as used herein, refers to the geographic location of the customer designated for delivery of the acetate tow band by any level of specificity including full address, continent, country, state, province, county, or city.

The term, "bale", as used herein, refers to a packaged unit of acetate tow bands, typically of a cubical shape, compressed to a high density, and wrapped, contained, and protected by packaging material. The term "bale identifier", as used herein refers to a code that can be correlated to the bale tracking system (e.g., bale number) used by the manufacturer of the acetate tow band.

The term, "warehouse" as used herein, refers to the geographical location of the warehouse designated for delivery of the acetate tow band by any level of specificity including full address, continent, country, state, province, country, or city.

The term, "correlating", as used herein refers to establishing the relationship between two or more pieces of information.

The term, "manufacturer specific taggants", as used herein, refers to the particular taggants incorporated into the acetate tow band by a particular manufacturer.

The term, "fibers are produced", "producing fibers", and "fiber production process", as used herein, refers to the process steps of spinning fibers up through the gathering of the fibers.

The term "concurrently to producing", as used herein, refers to process of surface marking identification fibers at the same time that the standard fibers are being produced, either prior to or after the identification fibers are combined with the standard fibers.

The term, "identification fibers are packaged", as used herein, refers to the process steps of transferring identification fibers from the spinning machine and packaging the identification fibers, for example, onto a spool or into a bale. The identification fibers would subsequently need to be removed from the package in order to be incorporated into the acetate tow band.

The term "fiber sample", as used herein, refers to the item comprising the acetate tow band, in any physical form, being analyzed using imaging technology. The fiber sample can comprise a portion of cigarette filter or filter rod which has been prepared for image analysis.

The terms, "imaging technology", and "image analysis techniques" as used herein, refer to the equipment and software used to detect and quantify differences in reflection, absorption, transmission, and emittance of electromagnetic radiation. Imaging technology encompasses both electromagnetic radiation level detection and automated pattern recognition.

In order to successfully tack and trace the supply chain of an acetate tow band, (1) a code needs to be incorporated into the acetate tow band, (2) the code needs to remain intact during blooming and other processing stresses that occur when the acetate tow band is incorporated into a filter, and (3) the code needs to be detectable (i.e., the identification fibers need to be located and separated from the rest of the fibers with the code still intact) in cigarettes found in the market place. We have surprisingly found that we can accommodate all three constraints by surface marking a set of identification fibers wherein the identification fibers comprise cellulose acetate. Making the identification fibers larger than the standard fibers facilitates both the surface marking and the locating and separating of the identification fibers.

The acetate tow band comprises fibers. The fibers comprise standard fibers and identification fibers. The standard fibers comprise cellulose acetate and the identification fibers comprise cellulose acetate. In other words, the identification fibers have the same chemical composition as the standard fibers. In one aspect, the acetate tow band consists of cellulose acetate fibers. The acetate tow band consists of cellulose acetate fibers is not meant to exclude the normal trace ingredients, such as titanium dioxide, or processing aids, such as lubricants widely found in acetate tow bands on the market.

The standard fibers comprise cellulose acetate for which size is often given in terms of denier per filament (dpf) which is defined as the weight, in grams, of a single filament 9000 meters in length. In one aspect, the size of the standard fibers ranges from, for example, 1.0 dpf to 30.0 dpf, 1.0 dpf to 20.0 dpf, 1.0 dpf to 15.0 dpf, 1.0 dpf to 10.0 dpf, 2.0 to 30.0 dpf, 2.0 dpf to 20 dpf, 2.0 dpf to 10.0 dpf, 3.0 dpf to 15.0 dpf, 3.0 dpf to 12.0 dpf, 3.0 dpf to 10.0 dpf, or 4.0 dpf to 10.0 dpf.

The total denier of the acetate tow band is not particularly limited. In one aspect, the total denier of the acetate tow band ranges from, for example, 5,000 denier to 100,000 denier, 5,000 denier to 80,000 denier, 5,000 denier to 60,000 denier, 5,000 denier to 40,000 denier, 6,000 denier to 100,000 denier, 6,000 denier to 80,000 denier, 6,000 denier to 60,000 denier, 6,000 denier to 40,000 denier, 7,000 denier to 100,000 denier, 7,000 denier to 80,000 denier, 7,000 denier to 60,000 denier, or 7,000 denier to 40,000 denier.

While both the identification fibers and standard fibers are cellulose acetate fibers, the identification fibers are larger than the standard fibers. This can be described in terms of a ratio of the size of the identification fibers to the size of the standard fibers. The ratio is calculated as the ratio of the denier per filament (dpf) of the identification fibers and standard fibers. The denier per filament of the identification fibers is represented as $dpf_{ID\ fibers}$. The denier per filament of the standard fibers is represented as $dpf_{STD\ fibers}$ and the ratio is represented as $dpf_{ID\ fibers}:dpf_{STD\ fibers}$. The ratio of the size of the identification fibers to the size of the standard fibers ($dpf_{ID\ fibers}:dpf_{STD\ fibers}$) is 1.5:1 or greater. In other aspects, ($dpf_{ID\ fibers}:dpf_{STD\ fibers}$) ranges from 1.5:1 to 10:1 or 1.5:1 to 5:1 or 1.5:1 to 3:1 or 1.5:1 to 2:1.

In one aspect, the denier per filament of the identification fibers ($dpf_{ID\ fibers}$) ranges from 1.5 dpf to 50.0 dpf, 1.5 dpf to 40.0 dpf, 1.5 dpf to 30.0 dpf, 1.5 dpf to 20.0 dpf, 5.0 to 50.0 dpf, 5.0 dpf to 30.0 dpf, 5.0 dpf to 10.0 dpf, 8.0 dpf to 30.0 dpf, 8.0 dpf to 20.0 dpf, 8.0 dpf to 18.0 dpf, 10.0 dpf to 20.0 dpf, or 15.0 dpf to 20.0 dpf.

Identification fibers exhibit one or more taggant surface markings wherein the taggant surface markings form a repeated pattern along the length of the identification fibers. The repeated pattern can be representative of a code which can correlate to information such as, for example, a bale identifier. One skilled in the art recognizes that a set of identification fibers comprising cellulose acetate would need to be incorporated into the acetate tow band because of the relative weakness of a monofilament of cellulose acetate fiber. A monofilament of cellulose acetate fiber does not have the strength required to survive the processing steps of applying the surface markings to the fiber and combining the identification fibers and the standard fibers into an acetate tow band. In one aspect, the total denier of the identification fibers ranges from, for example, 30 denier to 300 denier, 30 denier to 200 denier, 30 denier to 150 denier, or 50 denier to 100 denier.

In one aspect, the identification fibers are processed parallel to one another from gathering after initial spinning, through applying the surface markings, to combining the identification fibers with the standard fibers to form the acetate tow band. "Processed parallel to one another" means that no special processing step to interlock the fibers into a yarn, such as twisting or entangling of the identification fibers, is performed. An acetate tow band is made by combining ends from the spinning cabinets. As such, the identification fibers which have been processed parallel to one another are analogous to the ends that are combined to make an acetate tow band.

In one aspect, the identification fibers have a crenulated cross-section. One skilled in the art recognizes that this is the cross-section of a cellulose acetate fiber that has been spun from a round cross-section hole. The crenulated cross-section gives a most rounded, regular shape to the cross-section for ease of applying surface markings. In one aspect, one or more of the identification fibers have a cross-section shape distinct from the remaining identification fibers and the remaining identification fibers have a crenulated cross-section. The identification fibers with a distinct cross-section shape may be used, for example, to readily identify a manufacturer of the acetate tow band.

In some aspects, the repeated pattern comprises an alphanumeric code, a digital code, an analog code, or an ideographic code. In some aspects, the repeated pattern comprises an alphanumeric code or a digital code. In some aspects, the repeated pattern comprises a digital code.

The repeated pattern along the length of the identification fibers may include metadata. The metadata can be useful in reading the pattern on the identification fibers. The metadata can be especially useful if the length of the identification fiber incorporated into a cigarette filter is approximately the same size or smaller than the length of the repeated pattern. In one aspect, the metadata comprises read-start position, read-end position, read direction, and/or the spacing of the digits within the code. Meta-data can also be used to give the manufacturer of the acetate tow band.

The digital code of the repeated pattern is not particularly limited. In some aspects, the pattern is in the form of a bar code, either a 1-D linear or 2-D matrix type code. In some aspects, the pattern could be a visual representation of a Morse code. In one aspect, the digital code comprises a binary code. In one aspect, the repeated pattern is essentially one-dimensional.

In one aspect, the digital code is a binary coding system, the two conditions or characters of each binary digit can be the presence or absence of a surface marking in a digit or location. In an alternative aspect, the two conditions could be one of two different surface markings in a digit. In some aspects, the digital code could be a binary representation of a place-value system of base x, where x is a power of 2 (or a binary). In one aspect, for example, when large number of combinations or integer values is to be coded, a hexadecimal (base 16) numbering system can be used to provide a notation that is more compact than a simple binary string. In a non-limiting illustration of such a hexadecimal system, 4 binary digits could make up each digit of the hexadecimal code, providing the 16 combinations or conditions for each of the hexadecimal digits. Base-x numbering systems can also be represented by x-number of unique surface markings in any digit or spacial location. In a non-limiting example, 5 different color dots can form the basis of a base-5 numbering system.

Multiple numbering or coding systems may be used in a single string of encoded information. In some aspects, the repeated pattern can contain a portion of binary coding with the sequence used to represent the manufacturer of the acetate tow band and another portion of the pattern that is a binary representation of a hexadecimal system used to represent unique bale identifiers of the manufacturer.

One skilled in the art recognizes that the selection of the number of digits for the binary code depends upon the complexity of information being captured and the space available for the taggant surface markings. In one aspect, the number of digits in the binary code ranges from 2 to 500. In other non-limiting examples, the number of digits in the binary code ranges from 4 to 100, 10 to 100, 20 to 100, 4 to 50, 10 to 50, or 20 to 50.

One skilled in the art also recognizes that the length of the repeated pattern on the identification fibers may be influenced by the length the fiber incorporated in typical articles. In one aspect, the length of the repeated pattern ranges from 2 mm to 500 mm. In other non-limiting examples, the length of the repeated pattern ranges from 2 to 200 mm, 2 to 30 mm, 10 to 200 mm, or 10 to 30 mm.

The manner in which the repeated pattern appears on the identification fiber is not particularly limited, so long as the pattern is recognizable. Non-limiting examples of how the repeated pattern is incorporated on the identification fibers include printing, engraving, morphological modifications of the fiber, or chemically producing a pattern of optical properties.

In some aspects, the identification fibers are readily separated from the standard fibers by physically segregating the identification fibers from the standard fibers.

An article can comprise the acetate tow band In one aspect, the article comprises a filter rod. In another aspect, the article comprises a cigarette filter.

The acetate tow band, filter rod, and/or cigarette filter have determinable supply chain information. The supply chain information can include manufacturer, manufacture site, manufacturing line, production run, production date, package, bale, warehouse, customer, and/or ship-to location. One skilled in the art recognizes that acetate tow manufacturers track bales and that identification of a particular bale allows for the retrieval of the types of supply chain information listed above.

The following is a non-limiting illustration of a possible binary coding system that demonstrates the ability to create many different code combinations on the branded fiber contained within a typical cigarette filter.

In the work of Example 1 below, the length of the crimped cellulose acetate identification fibers within a typical 21 mm length cigarette filter was shown to be approximately 25.2 mm. In addition, a spacing of laser engraving marks of 0.5 mm was shown to be readily achievable using the laser system of the example. Such a spacing applied to a 25 mm fiber length would allow up to 50 bits or digits to be encoded on the identification fiber within each cigarette filter. Each bit would contain binary-type (0 or 1) information corresponding to existence or non-existence of a printed mark (or laser etch) within the space.

In order to eliminate translational and rotational decoding errors in decoding, metadata in the form of a header may be desired with the coded sequence. The header could provide read start and read direction information. Such a header would allow for the reliable decoding of any one cigarette filter with a coding frequency as low as one code per cigarette filter. The header could take the form of a binary sequence designed such that it could not be confused with the characters of the code itself. For example, for a hexadecimal system in binary notation, the 10 bit sequence 0011111010 might be used. In one aspect, the header simply has taggant surface markings distinct from any of the taggant surface markings in the remainder of the code.

Of the remaining 40 bits of the 50 bits available of this example, 39 bits could be used to express 8 hexadecimal characters in binary (8×4 digits, plus spaces between each 4-digit character) to encode a sequence that would take the form (####_####_190 ###_####_####_####_####_####). With this format, 4,294,967,296 unique codes could be generated or, by using standard binary numbering, the numbers 0 to 4,294,967,295 could be generated. These codes or numbers could be correlated to supply chain information, such as bale numbers.

To further illustrate the example, the number 4,294,967,295 would be converted to its hexadecimal binary form 1111011110111101111011110111101111. The complete code, including the header, would be 00111110101111011110111101111011110111101111.

The current world-wide demand for acetate tow for cigarette filtration is approximately 700,000,000 kg per year. Assuming an average bale weight of 500 kg, the total number of bales produced in one year is approximately 1.4M. The implementation of a surface marking coding system of this example could therefore encode supply chain information at the bale level for over 3000 years' worth of production. In some aspects, fewer digits are used in each code and typical cigarette filters contain more than one repeated pattern of taggant surface markings.

In another embodiment, a method of making an acetate tow band comprises: (a) obtaining the identification fibers; (b) producing the standard fibers on a first fiber production process; and (c) combining the identification fibers and the standard fibers into the acetate tow band. The fibers comprise standard fibers and identification fibers. The standard fibers and identification fibers comprise cellulose acetate. A ratio of a size of the identification fibers to a size of the standard fibers ($dpf_{ID\ fibers}$:$dpf_{STD\ fibers}$) is 1.5:1 or greater. The identification fibers exhibit one or more taggant surface markings. The taggant surface markings form a repeated pattern along a length of the identification fibers. The taggant surface markings and the repeated pattern are representative of a bale identifier of the acetate tow band.

Embodiments of a method of making an acetate tow band encompass acetate tow bands comprising fibers with any combination of attributes disclosed above. Specifically, the sizes of standard fibers, the total denier of the acetate tow band, the sizes of identification fibers, the total denier of the identification fibers, the ratio of the size of the identification fibers to the size of the standard fibers ($dpf_{ID\ fibers}$:$dpf_{STD\ fibers}$), the identification fibers being parallel to one another, the shapes of the identification fibers, the surface markings, the repeated patterns, the length of the repeated patterns, the supply chain information, and the non-limiting coding/correlation systems apply to the method of making the acetate tow band.

The standard fibers are produced on a first fiber production process. Obtaining the identification fibers comprises at least one of (i) producing of a portion of the identification fibers on a second fiber production process followed by applying the taggant surface markings in the repeated pattern to the identification fibers (ii) receiving a portion of the identification fibers from a third party followed by applying the taggant surface markings in the repeated pattern to the identification fibers, or (iii) receiving a portion of the identification fibers having the taggant surface markings in the repeated pattern from the third party.

When and where the identification fibers are surface marked is not particularly limiting. In some aspects, the surface markings can be applied prior to the identification fibers and standard fibers being combined or, at least, prior to subsequent processing of the combined fibers, such as prior to crimping. In some aspects, the identification fibers are produced separately from the standard fibers on a separate spinning process, the surface markings can be applied at any time prior to their combining with the standard fibers, including by a third party, or concurrent with their combining with the standard fibers.

Non-limiting examples of methods of surface marking the identification fibers include printing, engraving, morphological modification, and chemically producing a pattern of optical properties. In some aspects, the printing of the surface markings could be performed using a commercial high-speed printer, such as an ink-jet printer, or a custom printer designed for the purpose. The printing can be performed with a single ink of one color or with multiple ink colors. In some aspects, engraving could be performed by contact equipment, such as equipment that uses abrasive surfaces, blades, or embossing rollers, or by noncontact equipment, such as lasers or other high energy radiation sources. In some aspects, a morphology modification can be performed by contact equipment, such as equipment that uses abrasive surfaces, or by noncontact equipment such as lasers or other high energy radiation sources.

In some aspects identification fibers are produced on a second fiber production process followed by applying the taggant surface markings in the repeated pattern. In some aspects, fibers are received from a third party. The taggant surface markings in the repeated pattern can be applied to the fibers to produce identification fibers any time before the identification fibers are combined with the standard fibers into an acetate tow band. The manner in which the taggant surface markings in the repeated pattern is applied to the branded fibers is not particularly limited. In some aspects, the taggant surface markings in the repeated pattern are printed on the identification fibers concurrently to producing the standard fibers. In some aspects, the taggant surface markings in the repeated pattern are laser engraved on the branded fibers concurrently to producing the standard fibers. In some aspects, the concurrently produced identification fibers and the standard fibers are combined prior to crimping the acetate tow band.

In one aspect, the identification fibers are produced on the first fiber production process. The identification fibers can be produced in one cabinet of the multi-cabinet acetate tow production process while the standard fibers are produced in the other cabinets. The identification fibers can be spun, gathered, and have surface markings applied to them before they are combined with the rest of the fiber ends from the other cabinets (i.e., before they are combined with the standard fibers).

The marking of the identification fibers concurrent with the production of (or the combining with) the standard fibers can be advantageous as it reduces complexity of managing and inventorying of pre-marked fibers and routing those identification fibers to designated production lines at the right time to ensure proper coding of the acetate tow band. In contrast, concurrent marking of the identification fibers can be readily controlled by standard computer systems (e.g., a PLC or a DCS), with the coding changed automatically and essentially instantaneously to code the bale identifier for the acetate tow band being produced.

The spinning process used for producing the cellulose acetate fibers for acetate tow bands is well known to one skilled in the art.

FIG. 1 shows a schematic process flow diagram of a non-limiting embodiment of applying surface markings to identification fibers while coproducing acetate tow fibers and combining them into an acetate tow band. Acetate tow band 112 is produced in manufacturing environment 100. Cellulose acetate spinning solution 102 is fed to fiber spinning process 120 where it is fed to several spinning cabinets, each with several spinnerets (not shown). The standard fibers 108 exiting each spinning cabinet, often called ends, are gathered together to form a band which is fed into a crimper 130. Identification fibers 104 pass under marking device 110 which imparts surface markings in a repeated pattern to produce identification fibers 106. Non-limiting examples of marking device 110 include a printer and a laser. Identification fibers 106 and standard fibers 108 are gathered together and fed to crimper 130 to produced crimped acetate tow band 112.

In yet another embodiment, a method of characterizing a cigarette filter is disclosed. The cigarette filter comprises an acetate tow band and the acetate tow band comprises fibers. The fibers comprise standard fibers and identification fibers. The standard fibers and identification fibers comprise cellulose acetate. A ratio of a size of the identification fibers to a size of the standard fibers ($dpf_{ID\ fibers}$:$dpf_{STD\ fibers}$) is 1.5:1 or greater. The identification fibers exhibit one or more taggant surface markings. The taggant surface markings form a repeated pattern along a length of the identification fibers. The method comprises (a) locating the identification fibers by exploiting the ratio of the size of the identification fibers to the size of the standard fibers; (b) separating the identification fibers from the cigarette filter; (c) applying imaging technology to at least one of the identification fibers; (d) detecting the taggant surface markings; (e) determining the repeated pattern of the taggant surface markings, wherein the taggant surface markings and the repeated pattern are representative of at least one supply chain component of the acetate tow band; and (f) generating, based on the detection and determination, supply chain information correlating the taggant surface markings and the repeated pattern to at least one supply chain component of the acetate tow band.

Embodiments of methods of characterizing a cigarette filter encompass cigarette filters comprising acetate tow bands comprising fibers with any combination of attributes disclosed above. Specifically, the sizes of standard fibers, the total denier of the acetate tow band, the sizes of identification fibers, the total denier of the identification fibers, the ratio of the size of the identification fibers to the size of the standard fibers ($dpf_{ID\ fibers}$:$dpf_{STD\ fibers}$), the identification fibers being parallel to one another, the shapes of the identification fibers, the surface markings, the repeated patterns, the length of the repeated patterns, the supply chain information, and the non-limiting coding/correlation systems apply to the method of characterizing the cigarette filter.

The process of characterizing a cigarette filter comprises (a) locating the identification fibers by exploiting the ratio of the size of the identification fibers to the size of the standard fibers and (b) separating the identification fibers from the cigarette filter. One skilled in the art of making filter rods/cigarette filters comprising acetate tow bands is familiar with testing newly made filter rods to assess whether the acetate tow has sufficient bloom. The newly-made filter rod has its wrapper paper removed and filaments separated to observe the bloom of the acetate tow band. The plasticizer has not dried or hardened when the filaments are separated from the newly-made filter rod. We have surprisingly found that we can locate and separate identification fibers with surface markings from cigarette filters long after the plasticizer has dried and hardened. Small sections of filaments can be separated from the cigarette filter. These can be divided into smaller sections if desired. When a section of filaments includes the identification fibers, the identification fibers are detected by their larger size than the standard fibers. The higher the ratio of a size of the identification fibers to a size of the standard fibers ($dpf_{ID\ fibers}$:$dpf_{STD\ fibers}$), the more readily and quickly the identification fibers can be located. Once the identification fibers are located, they can be readily separated from the standard fibers. In one aspect, the method comprises physically segregating the identification fibers from the rest of the cigarette filter.

In one aspect, the imaging technology comprises the use of electromagnetic radiation at visible wavelengths. In another aspect, the image technology comprises the use of electromagnetic radiation at invisible wavelengths. The equipment useful for imaging technology is not particularly limited. Non-limiting examples include visual inspection, magnification, microscopy, electron microscopy, confocal microscopy, and optical scanning.

The imaging technology can be applied to the fiber sample parallel to the length of the identification fibers. This direction allows, for example, a view of a pattern of surface markings on the identification fibers.

The method of characterizing a cigarette filter comprises (d) detecting the taggant surface markings and (e) determining the repeated pattern of the taggant surface markings. The taggant surface markings and the repeated pattern are representative of at least one supply chain component of the acetate tow band. The at least one supply chain component comprises a bale identifier and/or a manufacturer.

The method of characterizing a cigarette filter comprises (f) generating, based on the detection and determination, supply chain information correlating the taggant surface markings and the repeated pattern to at least one supply chain component of the acetate tow band.

The trace and track system can be set up in many different ways. In one scenario, a laboratory or other entity that characterizes the cigarette filter may only identify the manufacturer (e.g., the metadata may indicate the manufacturer). The manufacturer may then characterize the cigarette filter and generate a bale identifier. In another scenario, a laboratory or other entity may generate information correlating the taggant surface markings and repeated pattern to a bale identifier.

In one aspect, the method comprises correlating the repeated pattern of taggant surface markings to a database comprising manufacturing specific taggants, and wherein the at least one supply chain component comprises a bale of the acetate tow band.

Figure 5A:
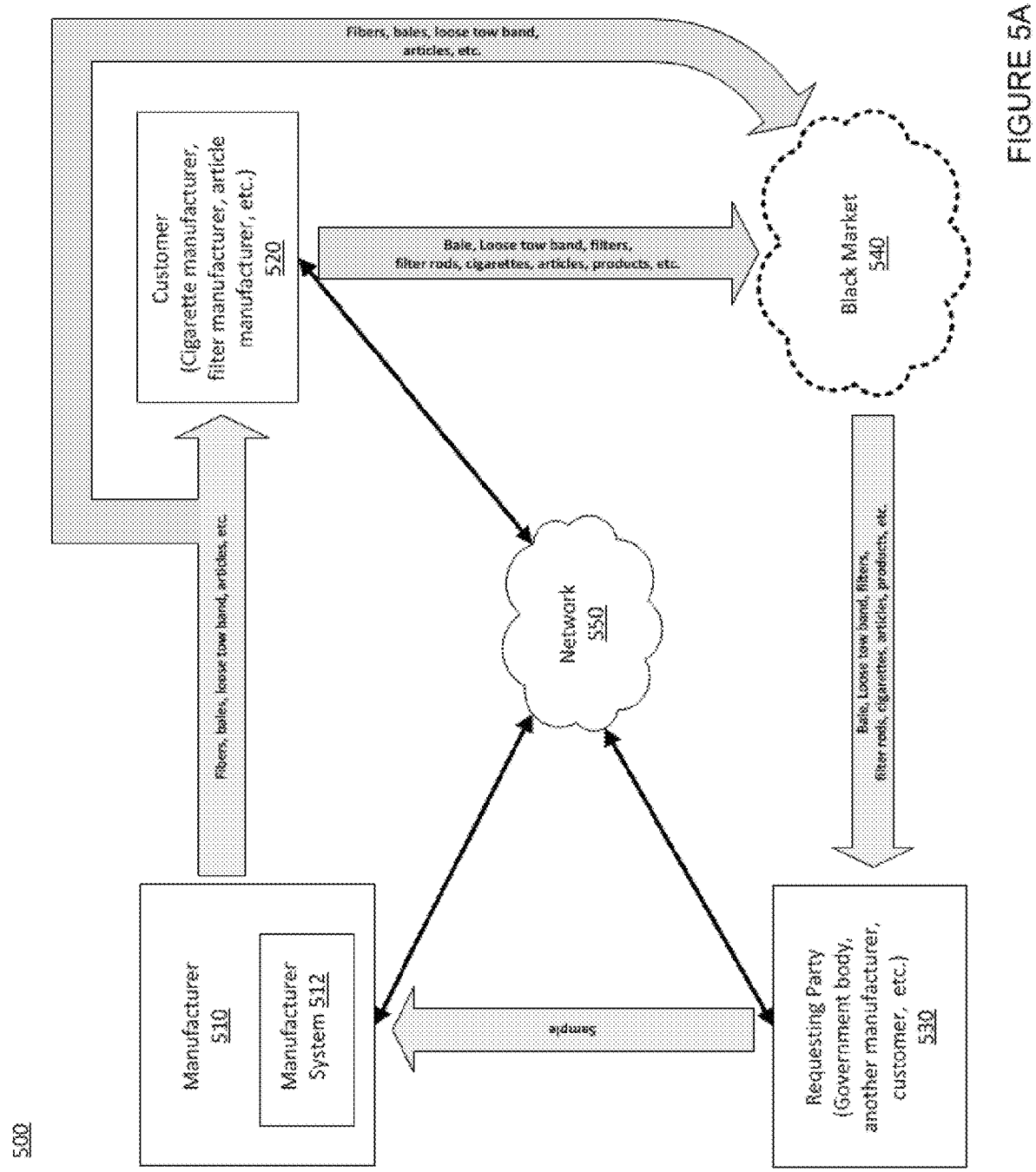
FIGS. 5A and 5B illustrate non-limiting examples of communication and shipping channels among one or more entities consistent with disclosed embodiments
Figure 5B:
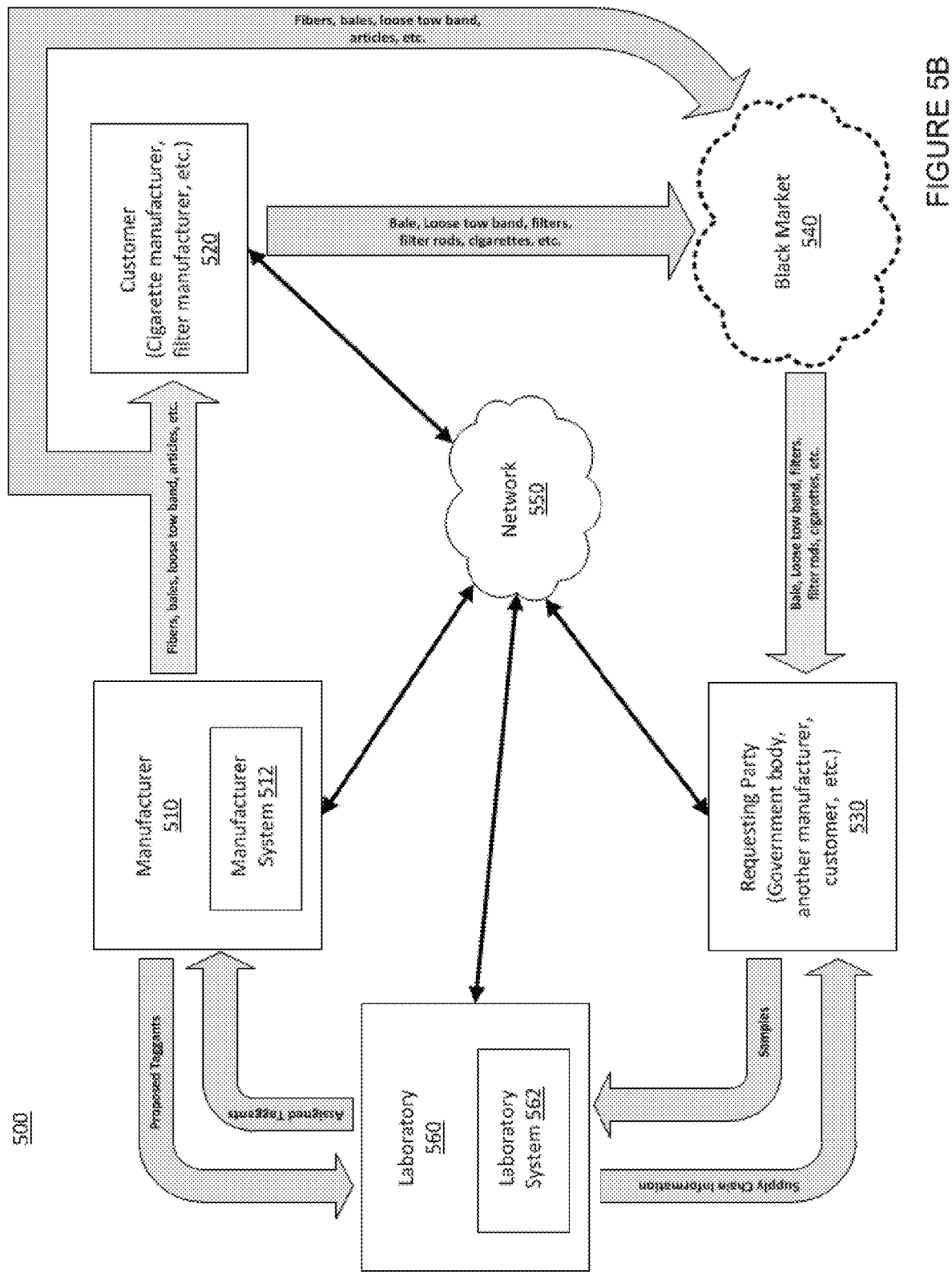

FIGS. 5A and 5B illustrate non-limiting examples of an environment 500 depicting communication and shipping channels among entities consistent with disclosed embodiments. In one embodiment, environment 500 of FIGS. 5A and 5B may include one or more manufacturers 510, one or more customers 520, a black market 540 or other illicit trade network, one or more requesting parties 530, one or more laboratories 560, and communication network 550. The components and arrangement of the components included in environment 500 (e.g., as illustrated in FIGS. 5A and 5B)

may vary. Thus, environment 500 may include other components that perform or assist in the performance of one or more processes consistent with the disclosed embodiments.

In some aspects, network 550 may be any type of network configured to provide communication means between systems of components of environment 500 (e.g., manufacturing system 512 and/or laboratory system 562). For example, network 550 may be any type of network (including infrastructure) that facilitates communications, exchanges information, etc., such as the Internet, a Local Area Network, near field communication, and/or other suitable connection(s) that enables the sending and receiving of information between the components systems associated with environment 500. In other embodiments, one or more component systems of environment 500 may communicate directly through a dedicated communication link(s), such as links between manufacturer 510, customer 520, requesting party 530, and/or laboratory 560.

Further, and as stated above, manufacturers (e.g., manufacturer 510) may produce cellulose acetate fibers and fiber products that incorporate the cellulose acetate fibers on an industrial scale. In some embodiments, the produced cellulose acetate fibers and fiber products may include standard fibers and identification fibers. Each of the identification fibers exhibits one or more distinct features (e.g., distinct surface markings.) that visually distinguish the identification fibers from the standard fibers. In some aspect, one or more of the distinct surface markings may represent a taggant surface markings, and the identification fibers may exhibit one or more of the taggant surface markings. The taggant surface markings exhibited by the identification fibers may, in certain aspects, form a repeated pattern disposed along the length of the identification fibers. The repeated pattern may, for example, be representative of at least one supply chain component associated with the standard fibers, the identification fibers, and/or fibers and fiber products that include the standard and/or identification fibers.

In other aspects, the repeated pattern may be representative of a code associated with the identification fibers and/or the standard fibers (e.g., an alphanumeric code, a digital code, an analog code, and/or an ideographic code, as described above). In some embodiments, portion of the code may be representative of at least one supply chain component associated with the standard fibers, the identification fibers, and/or fibers and fiber products that include the standard and/or identification fibers.

In some embodiments, the inclusion of identification fibers in the cellulose acetate fibers may enable manufacturer 510 to tag the cellulose acetate fibers, and thus, the fiber products that include the cellulose acetate fibers, with supply chain information prior to shipment to customers 520. By way of example, fiber products consistent with the disclosed embodiments may include, but are not limited to, cellulose acetate tow, loose bands of cellulose acetate tow, bales of cellulose acetate tow, and fabrics and other articles that include the cellulose acetate fibers and/or tow.

For example, and in the context of cigarette manufacturing, customer 520 may use a bale of acetate tow to produce various intermediate and/or final stage products (e.g., loose tow band, filter rods, filters, and/or cigarettes) and a fraction of these products can ultimately find their way onto the black market (e.g., black market 440). Thus, because supply chain information can be determined from a sample of any black-market product having tagged identification fibers, a party interested in combating illicit trade (e.g., requesting party 530) may obtain a black-market product and submit a sample for analysis in order to identify supply chain information associated with the black-market product.

Thus, in one embodiment, requesting party 530 may provide the sample to manufacturer 510, as depicted in FIG. 5A. Manufacturer 510 may, in certain aspects, analyze the sample using any of the exemplary techniques outlined above to identify at least one component of a supply chain associated with the sample. For example, the sample may include standard and identification fibers which exhibit one or more taggant surface markings that form a repeated pattern along a length of the identification fibers. Based on the analysis, manufacturer 510 may identify the one or more identification fibers that exhibit the one or more taggant surface markings. Manufacturer 510 may also identify the repeated pattern formed by the taggant surface markings along the length of the identification fibers (e.g., through an application of an imaging technology to the identification fibers, as described above).

In certain aspects, manufacturer 510 may access correlation data mapping components of the supply chain to the exhibited taggant surface markings and additionally or alternatively, to the identified repeated pattern formed by the taggant surface markings along the length of the identification fibers. Manufacturer 510 may identify the at least one component of the supply chain based on, for example, a comparison of the exhibited taggant surface markings and/or the identified repeated pattern to the accessed correlation data. In some instances, manufacturer 510 may transmit information identifying the at least one supply chain component to requesting party 530 (e.g., across network 550).

In the exemplary embodiments described above, manufacturer 510 may analyze the sample to identify at least one component of a supply chain associated with the sample. The disclosed embodiments are, however, not limited to exemplary analyses conducted by manufacturer 510, and in further embodiments, customer 520, requesting party 530, or a third-party (not shown) may conduct the analysis for identifying supply chain information from tagged fibers.

For example, as illustrated in FIG. 5B, a laboratory 560 may act on behalf of requesting party 530 and perform the analysis on the sample to identify the at least one supply chain component associated with the sample. In some instances, laboratory 560 may represent a governmental entity, a quasi-governmental entity, or a private entity capable of performing the analysis, and requesting party 530 may contract with or retain laboratory 560 to perform the analysis on a one-time or recurring basis.

In other instances, however, laboratory 560 may be established by one of more of manufacturer 510, customers 520, and/or requesting party 530 in order to regularly and reliably identify supply chain components associated with samples taken from illicitly traded cellulose acetate fibers or fiber products that incorporate the cellulose acetate fibers (e.g., as obtained by requesting party 530 from black market 540). Laboratory 560 may, in certain aspects, perform the analysis of the sample in accordance with one or more procedures established by a manufacturer 510, customers 520, and/or requesting party 530. For example, one or more of manufacturer 510, customers 520, and/or requesting party 530 may collectively establish standardized procedures and protocols for receiving and handling samples, analyzing the samples to identify the supply chain components in an accurate and repeatable manner, and reporting portions of the identified supply chain components to manufacturer 510, customers 520, and/or requesting party 530. Further, in additional embodiments, laboratory 560 may also assign the taggant surface markings, repeated patterns formed by taggant surface markings, and/or portions of the codes represented by the repeated patterns to various components of the supply chain (e.g., manufacturers) to uniquely identify these supply chain components. In further embodiments, customer 520, requesting party 530, or a third-party (not shown) may assign the taggant surface markings, repeated patterns formed by taggant surface markings, and/or portions of the codes represented by the repeated patterns to various components of the supply chain (e.g., manufacturers) to uniquely identify these supply chain components.

In one embodiment, as illustrated in FIG. 5B, requesting party 530 may provide the sample to laboratory 560. Laboratory 560 may, in certain aspects, analyze the sample to identify at least one component of a supply chain associated with the sample (e.g., a manufacturer). For example, using any of exemplary techniques described above, laboratory 560 may analyze the sample to identify the identification fibers that exhibit one or more taggant surface markings. Laboratory 560 may further identify one or more repeated patterns formed by the taggant surface markings along the length of the identification fibers. Further, laboratory 560 may access correlation data, and using any of the exemplary techniques described above, identify the at least one supply chain component based on a comparison of the exhibited taggant surface markings and the identified repeated patterns to the accessed correlation data.

In additional embodiments, laboratory 560 may function as a centralized facility that assigns unique taggant surface markings, unique repeated patterns, and unique codes (or portions of codes) represented by the repeated patterns to various components of the supply chain (e.g., to manufacturer 510). For example, laboratory 560 may assign, to manufacturer 510, a taggant surface marking, a repeated pattern formed by the assigned taggant surface marking, and/or a portion of a code represented by the assigned repeated pattern.

When exhibited by identification fibers included within cellulose acetate fibers and corresponding fiber products produced by manufacturer 510, the assigned taggant surface marking, assigned repeated pattern, and/or assigned code portion may uniquely represent manufacturer 510 and may enable laboratory 560 (and additionally or alternatively, any other entity within environment 500) to identify manufacturer 510 as a source of the fibers or fiber products using any of the analytical techniques described above. Further, laboratory 560 (and additionally or alternatively, any other entity within environment 500) may also establish and maintain data records (e.g., within a centralized database implemented using the exemplary computing systems outlined below) that identify a correlation between the various supply chain components (e.g., manufacturer 510) and corresponding ones of the assigned taggant surface markings, repeated patterns, and/or code and code portions.

The disclosed embodiments are, however, not limited to the assignment of exemplary taggant surface markings, exemplary repeated patterns, and/or exemplary code and code portions to manufacturer 510. In further embodiments, laboratory 560 may assign any additional or alternate taggant information, and further, any additional or alternate set or combinations of sets of taggant surface markings, repeated patterns, and/or code and code portions to uniquely identify manufacturer 510.

In certain aspects, laboratory 560 may establish a centralized repository for data and data records (e.g., using any of the exemplary computing systems outlined below) that correlate the various supply chain components (e.g., manufacturer 510) to corresponding ones of taggant surface markings, repeated patterns formed by taggant surface markings, and/or codes and code portions represented by the repeated patterns. Further, in other aspects, laboratory 560 may access the centralized repository and generate one or more reports specifying the taggant surface markings, repeated patterns formed by the taggant surface markings, and/or codes represented by the repeated patterns that uniquely identify at least one of the supply chain components (e.g., manufacturers). Laboratory 560 may, in some instances, generate the reports at predetermined intervals or in response to received requests (e.g., from requesting party 530, manufacturer 510, etc.), and may provide the generated reports to various parties and entities within environment 500 (e.g., across network 550).

In some embodiments, laboratory 560 may access the centralized repository to identify at least one supply chain component (e.g., manufacturer 510) associated with taggant surface markings and/or a repeated patterns formed by the taggant surface markings determined by laboratory 560 (e.g., using any of the analytical techniques outlined above) and additionally or alternatively, obtained from any third party or other entity within environment 500. Further, and as described below, the centralized repository may enable laboratory 560 to determine whether proposed taggant surface markings, proposed repeated patterns capable of being formed by the taggant surface markings, and/or proposed codes representable by the repeated patterns (e.g., as selected by manufacturer 510) are capable of uniquely representing fibers and fiber products of manufacturer 510 that are introduced into the supply chain.

In certain embodiments, laboratory 560 may receive one or more proposed taggant surface markings, a proposed repeated pattern, and/or a proposed code (or code portion) representable by the proposed repeated pattern from manufacturer 510. Laboratory 560 may, for example, compare the proposed taggant surface markings, proposed repeated pattern, and/or proposed code (or code portion) against the established data records (e.g., within the centralized repository) to determine whether these proposed taggant surface markings, proposed repeated pattern, and/or proposed code (or code portion) are capable of uniquely identifying manufacturer 510 (e.g., the proposed taggant surface markings, proposed repeated pattern, and/or proposed code (or code portion) are assigned to no other supply chain components, such as another manufacturer). If the proposed taggant surface markings, proposed repeated pattern, and/or proposed code (or code portion) could uniquely represent manufacturer 510, laboratory 560 may assign the proposed taggant surface markings, proposed repeated pattern, and/or proposed code (or code portion) to manufacturer 510, update the data records to reflect the assignment, and provide confirmation of the assignment to manufacturer 510 (e.g., between computing systems of laboratory 560 and manufacturer 510 across network 550).

Alternatively, if laboratory 560 previously assigned the proposed taggant surface markings, proposed repeated pattern, and/or proposed code (or code portion) to another manufacturer (or the proposed taggant surface markings, proposed repeated pattern, and/or proposed code (or code portion) are inappropriate to represent manufacturer 510), laboratory 560 may assign one or more alternate taggant surface markings, an alternate repeated pattern, and/or an alternate code (or code portion) representable by the alternate repeated pattern to manufacturer 510, update the data records to reflect the alternate assignment, and provide confirmation of the alternate assignment to manufacturer 510. In other aspects, laboratory 560 could provide, to manufacturer 510, an indication of the assignment of the proposed taggant surface markings, proposed repeated pattern, and/or proposed code (or code portion) to another manufacturer, and request that manufacturer 510 propose one or more additional taggant surface markings, an additional repeated pattern, and/or an additional code (or code portion) representable by the additional repeated pattern for assignment by laboratory 560, as described above.

In certain aspects, upon confirmation of the assignment, manufacturer 510 may obtain and/or produce identification fibers exhibiting the assigned taggant surface markings, which form the assigned repeated pattern, and which represent the assigned code and/or code portion. In other aspects, however, manufacturer 510 may further correlate the assigned taggant surface markings, the assigned repeated patterns, and/or the assigned code (or code portion) represented by the assigned repeated patterns to one or more upstream components of the supply chain (e.g., a manufacture site, a manufacturing line, a production run, a production date, a bale) and/or various downstream components of the supply chain (e.g., a warehouse, a customer, a ship-to location, etc.). For example, manufacturer 510 may further specify that additional code or code portions associated with the assigned repeated pattern (i.e., code portions distinct from those representing manufacturer 510) uniquely represent a particular customer within the supply chain (e.g., customer 520) or a particular bale produced and shipped by manufacturer 510.

The disclosed embodiments are, however, not limited to techniques that enable manufacturer 510 to correlate customer 520 and/or a particular bale to the assigned taggant surface markings, the assigned repeated patterns, and/or the assigned code (or code portion) represented by the assigned repeated patterns. In further embodiments, manufacturer 510 may specify any additional or alternate taggant information (e.g., distinct features, combinations of distinct features, etc.) to represent other upstream or downstream supply components (or combinations thereof) in conjunction with the assigned taggant surface markings, the assigned repeated patterns, and/or the assigned code (or code portion) represented by the assigned repeated patterns.

In some aspects, while laboratory 560, or another entity, may maintain information linking manufacturer 510 to assigned taggant surface markings, the assigned repeated patterns, and/or the assigned code (or code portion) represented by the assigned repeated patterns, manufacturer 510 may hold confidential additional taggant information (e.g., distinct features, combinations of distinct features, non-assigned code portions, etc.) that links identification fibers, and thus fiber products produced by manufacturer 510, to other upstream and downstream components of the supply chain. The confidentiality of the additional taggant information may, in certain instances, enable manufacturer 510 to prevent laboratory 560 from identifying customers (e.g., customer 520), ship-to locations, warehouses, and other internal supply chain components (e.g., manufacture site or line, and production run or date) associated with manufacturer 510.

The embodiments described above identify particular combinations of taggant information that correlate to a specific component of a supply chain and, when exhibited in identification fibers of a sample, enable a laboratory, a manufacturer, or other entities to identify the specific supply chain component associated with the sample. One of ordinary skill in the art would, however, understand that the disclosed embodiments are not limited to the particular combinations or taggant information outlined above, and in further embodiments, specific supply chain components may be correlated with any additional or alternate physical, chemical, and/or optical characteristic exhibited by the identification fibers, which include, but are not limited to, distinct features, and/or combinations of distinct features. Moreover, while not depicted in FIGS. 5A and 5B, one of skill in the art would understand that entities associated with environment 500 (shown and not shown) may employ one or more warehouses to store raw materials, intermediate products, final stage products, etc. in conducting operations consistent with disclosed embodiments.

Further, the disclosed embodiments are, however, not limited to the assignment of taggant surface markings, repeated patterns, and/or codes and code portions to various components of the supply chain (e.g., manufacturers). In further embodiments, manufacturer 510, laboratory 560, customers 520, requesting party 530, or a third-party (not shown) may assign other taggant information to the various components of the supply chain, which include, but are not limited to, distinct features, and/or combinations of distinct features.

Figure 6:
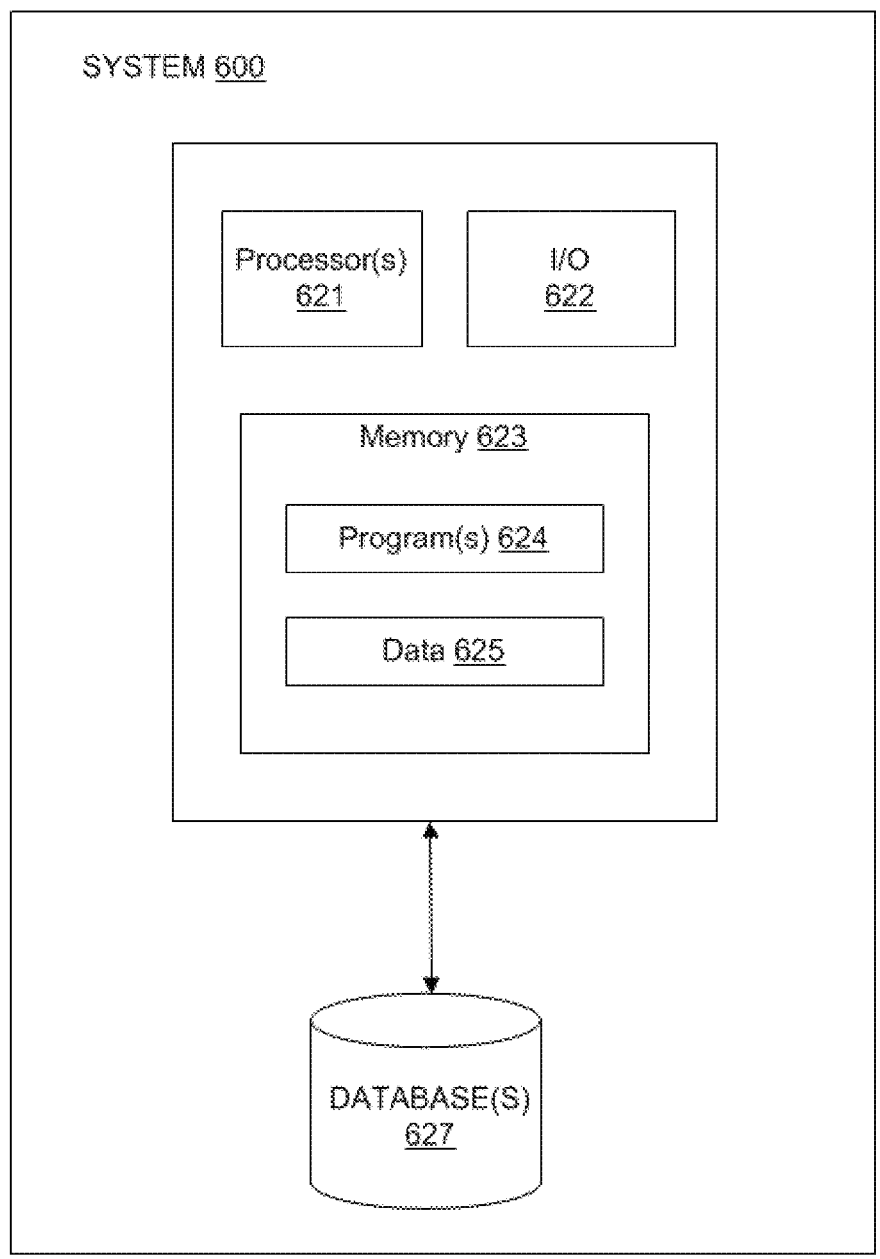
FIG. 6 illustrates a non-limiting example of a computing system used by one or more entities consistent with disclosed embodiments.

FIG. 6 illustrates a non-limiting example of a computing system 600 used by one or more entities consistent with disclosed embodiments. Variations of exemplary system 600 may be used by manufacturer 510 (e.g., as manufacturer system 512), customer 520, requesting party 530, and/or laboratory 560 (e.g., as laboratory system 562). In one embodiment, system 600 may comprise one or more processors 621, one or more input/output (I/O) devices 622, and one or more memories 623. In some embodiments, system 600 may take the form of a server, mainframe computer, or any combination of these components. In some embodiments, system 600 may take the form of a mobile computing device such as a smartphone, tablet, laptop computer, or any combination of these components. Alternatively, system 600 may be configured as a particular apparatus, embedded system, dedicated circuit, and the like based on the storage, execution, and/or implementation of the software instructions that perform one or more operations consistent with the disclosed embodiments.

Processor 621 may include one or more known processing devices, such as mobile device microprocessors or any various other processors. The disclosed embodiments are not limited to any type of processor(s) configured in system 600.

Memory 623 may include one or more storage devices configured to store instructions used by processor 624 to perform functions related to the disclosed embodiments. For example, memory 623 may be configured with one or more software instructions, such as program(s) 624 that may perform one or more operations consistent with disclosed embodiments when executed by processor 621. The disclosed embodiments are not limited to separate programs or computers configured to perform dedicated tasks. For example, memory 623 may include a single program 624 that performs the functions of system 600, or program 624 may comprise multiple programs. Memory 623 may also store data 625 that is used by one or more programs 612, such as correlation data mapping distinct features to one or more components of the supply chain information.

I/O devices 622 may be one or more devices configured to allow data to be received and/or transmitted by system 600. I/O devices 622 may include one or more digital and/or analog devices that allow components of environment 500 to communicate with other machines and devices, such as other components of environment 500. For example, I/O devices 622 may include a screen for displaying messages, distinct feature information, supply chain information, or providing other information to the user, such as an employee of manufacturer 510, customer 520, requesting party 530, and/or laboratory 560. I/O devices 622 may also include one or more digital and/or analog devices that allow a user to interact with system 600 such as a touch-sensitive area, keyboard, buttons, or microphones. I/O devices 622 may also include other components known in the art for interacting with a user.

The components of system 600 may be implemented in hardware, software, or a combination of both hardware and software, as will be apparent to those skilled in the art. For example, although one or more components of system 600 may be implemented as computer processing instructions, all or a portion of the functionality of system 600 may be implemented instead in dedicated electronics hardware.

System 600 may also be communicatively connected to one or more database(s) 627. System 600 may be communicatively connected to database(s) 627 through network 550. Database 627 may include one or more memory devices that store information and are accessed and/or managed through system 600. By way of example, database(s) 627 may include Oracle™ databases, Sybase™ databases, or other relational databases or non-relational databases, such as Hadoop sequence files, HBase, or Cassandra.

The databases or other files may include, for example, data and information related to distinct features, supply chain information, correlation data mapping the distinct features (e.g., taggant surface marking(s)), repeated pattern(s) formed by taggant surface markings, and/or code(s) associated with the repeated pattern(s) to the supply chain information, data indicative of distinct features (e.g., taggant surface marking(s)), repeated pattern(s) formed by taggant surface markings, and/or code(s) associated with the repeated pattern(s) assigned to the supply chain information, etc. For example, the databases and other files may include correlation data mapping the supply chain components to distinct features (e.g., taggant surface marking(s)), repeated pattern(s) formed by taggant surface markings, and/or code(s) associated with the repeated pattern(s) included in fiber samples, as described above. Further, by way of example, the databases and other files may also include distinct features (e.g., taggant surface marking(s)), repeated pattern(s) formed by taggant surface markings, and/or code(s) associated with the repeated pattern(s) included in fiber samples assigned to supply chain components by laboratory 560, as outlined above.

Systems and methods of disclosed embodiments, however, are not limited to separate databases. In one aspect, system 600 may include database 627. Alternatively, database 627 may be located remotely from the system 600. Database 627 may include computing components (e.g., database management system, database server, etc.) configured to receive and process requests for data stored in memory devices of database(s) 627 and to provide data from database 627.

Although the above description has designated laboratory 560 as the entity assigning various taggants, in other aspects, manufacturer 510, customer 520, requesting party 530 or a third-party entity not shown may be the one assigning taggants for identification fibers.

Figure 7:
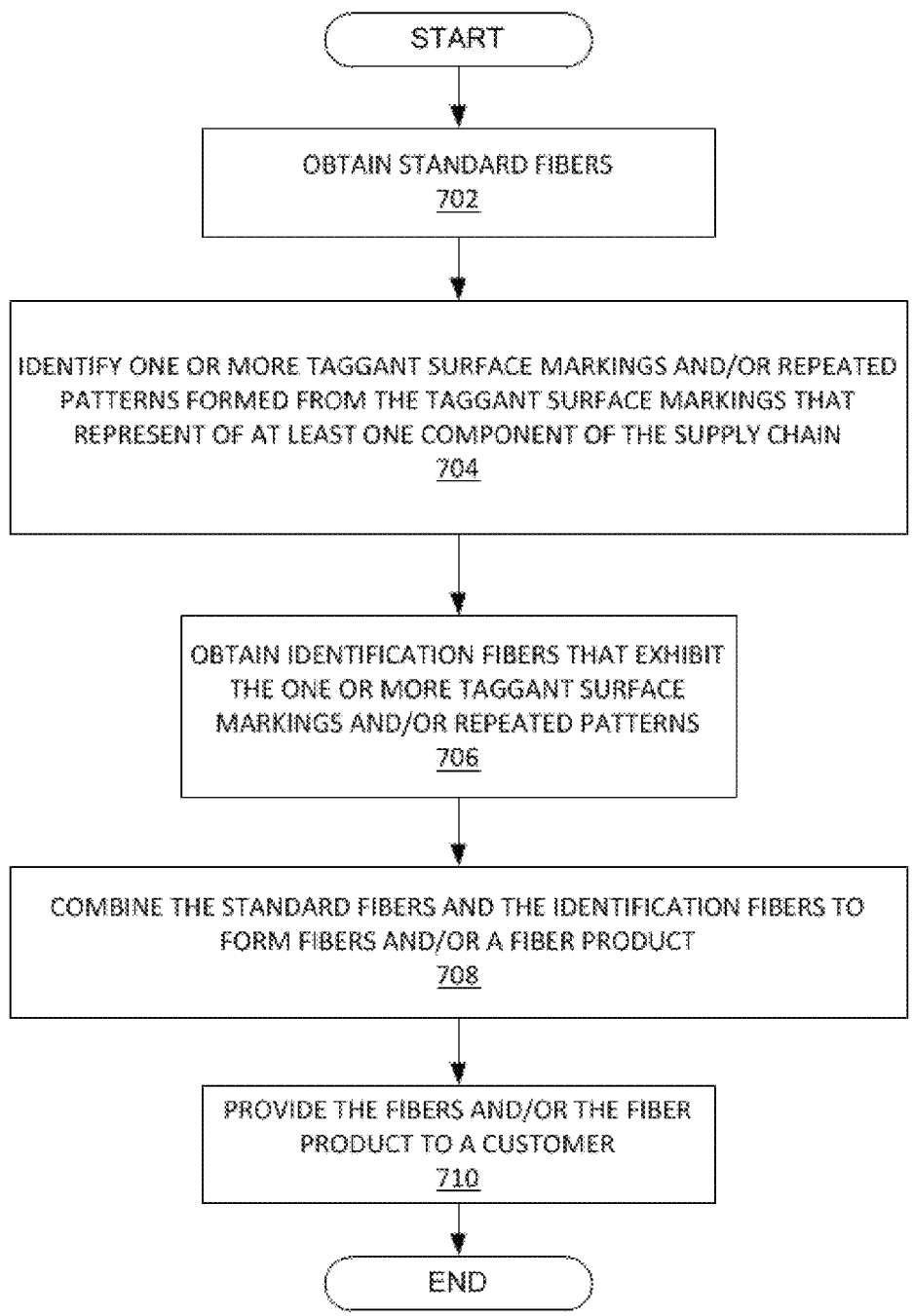
FIG. 7 illustrates a non-limiting example of a process for embedding supply chain information into fibers, consistent with disclosed embodiments.

FIG. 7 illustrates a non-limiting example of a process for embedding supply chain information into fibers, as seen and described above with respect to disclosed embodiments.

Figure 8:
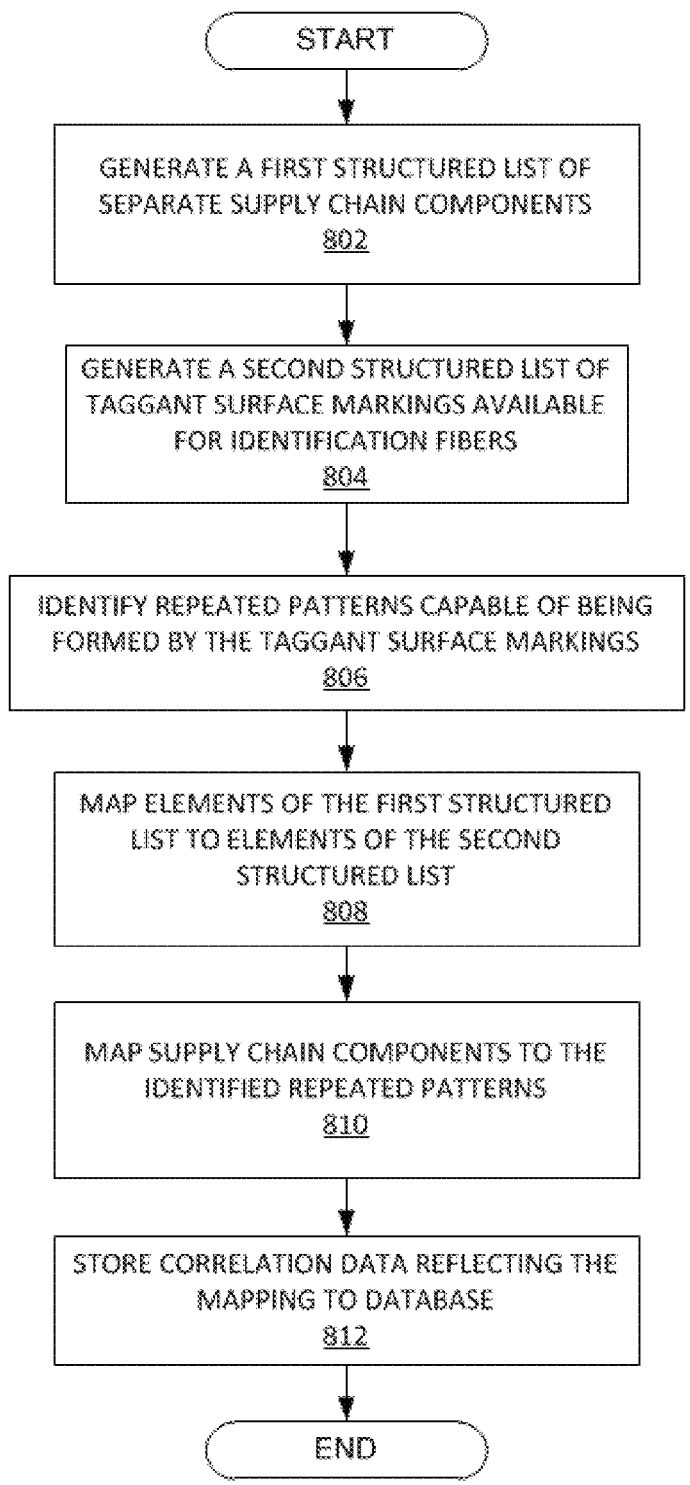
FIGS. 8 and 9 illustrate non-limiting examples of processes for generating correlation data, consistent with disclosed embodiments.

FIG. 8 illustrates a non-limiting example of a process for generating correlation data, as seen and described above with respect to disclosed embodiments. For example, as described in FIG. 8, manufacturer 510 (and additionally or alternatively, laboratory 560) may generate a first structured list of the supply chain components having one or more corresponding attributes, and may generate a second structured list of taggant surface markings available for application to or inclusion within identification fibers. In one instance, the supply chain components may represent one or more corresponding attributes. Manufacturer 510 may identify repeated patterns capable of being formed by the taggant surface markings along lengths of identification fibers. In some aspects, manufacturer 510 may map elements of the first structured list to elements of the second structured list, and may map the supply chain components of the first structured list to the identified repeated patterns. Manufacturer 510 may, in additional aspects, store correlation data (e.g., in database 627) reflecting the mapping of the elements of the first and second structured lists.

Figure 9:
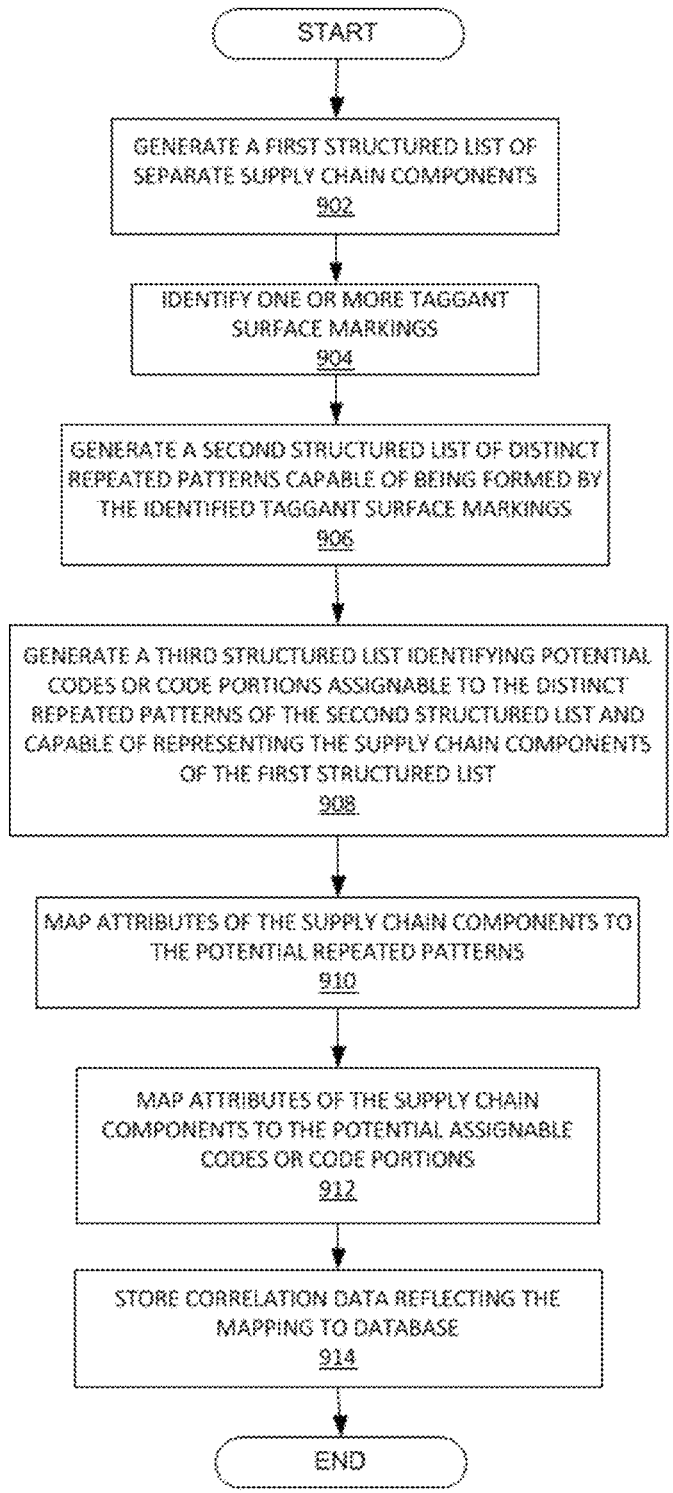

FIG. 9 illustrates an additional non-limiting example of a process for generating correlation data, as seen and described above with respect to disclosed embodiments. For example, as described in FIG. 9, laboratory 560 (and additionally or alternatively, manufacturer 510) may generate a first structured list of components of the supply chain. In one instance, the supply chain components may represent one or more corresponding attributes. Laboratory 560 may also identify one or more taggant surface markings appropriate for application to or inclusion within identification fibers (i.e., branded fibers), and may generate a second structured list that includes potential repeated patterns capable of being formed by the identified taggant surface markings. In some aspects, laboratory 560 may generate a third structured list identifying potential codes or code portions that are assignable to the potential repeated patterns of the second structured list and capable of representing the supply chain components of the first structured list. Laboratory 560 may further map elements of the first structured list to elements of the second structured list, and further map elements of the first structured list to elements of the third structured list. In some aspects, laboratory 560 may store correlation data (e.g., in database 627) reflecting the mappings of the attributes of the supply chain components to the potential repeated patterns and potential code and code portions.

Figure 10:
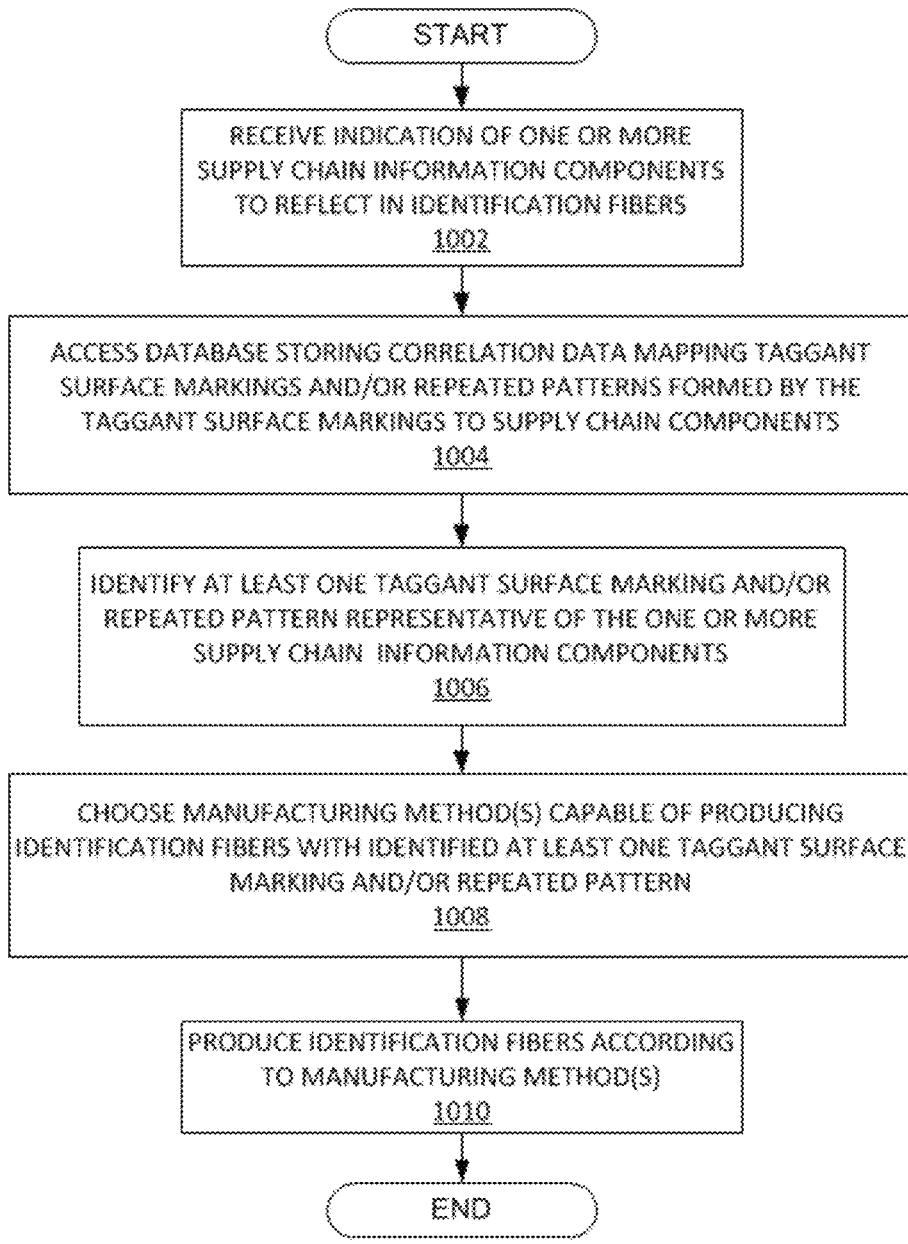
FIG. 10 illustrates a non-limiting example of a process for producing identification fibers, consistent with disclosed embodiments.

FIG. 10 illustrates a non-limiting example of a process for producing identification fibers, as seen and described above with respect to disclosed embodiments.

Figure 11:
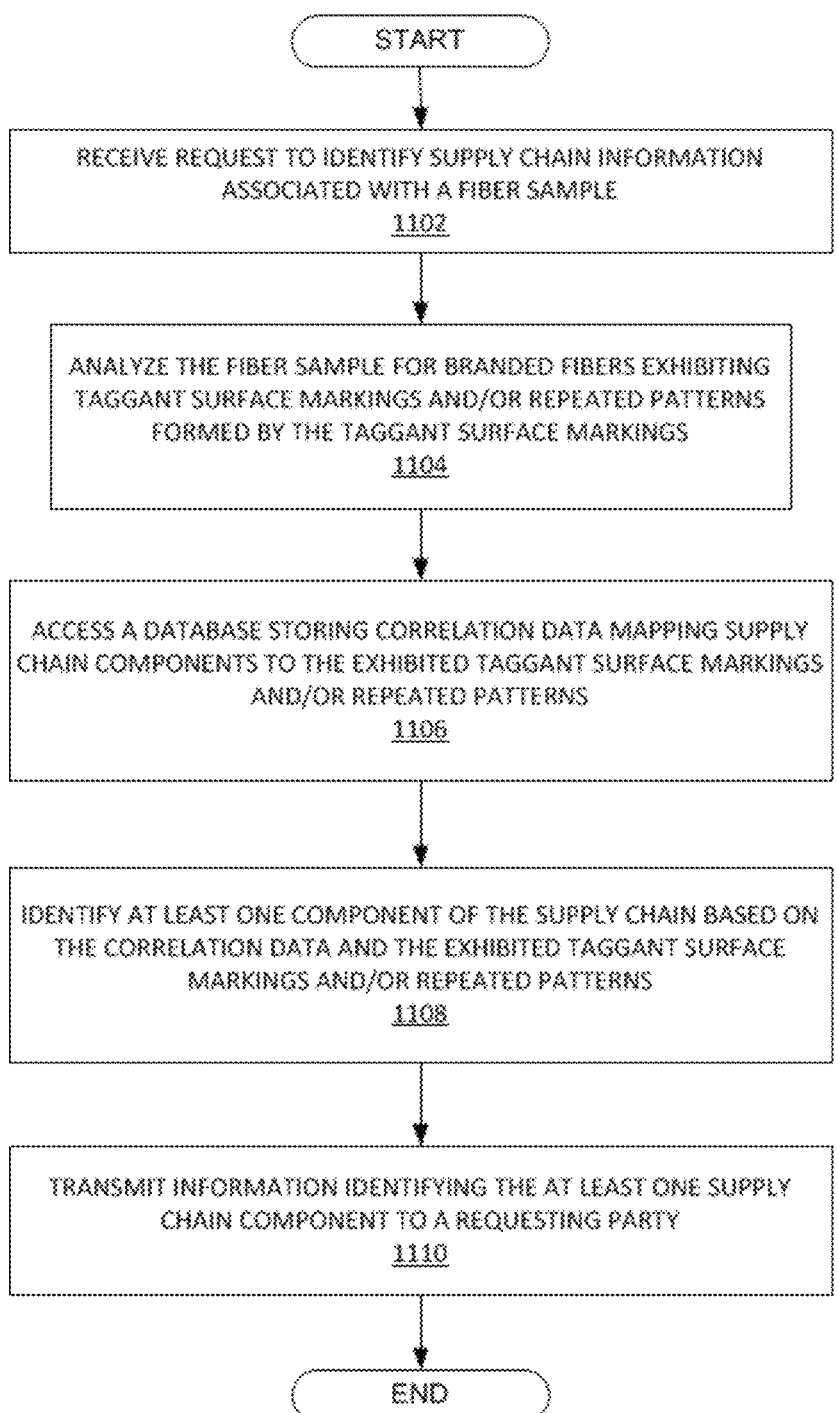
FIG. 11 illustrates a non-limiting example of a process for identifying supply chain information from a sample, consistent with disclosed embodiments.

FIG. 11 illustrates a non-limiting example of a process for identifying at least one supply chain component associated with a fiber sample, as seen and described above with respect to disclosed embodiments.

Figure 12:
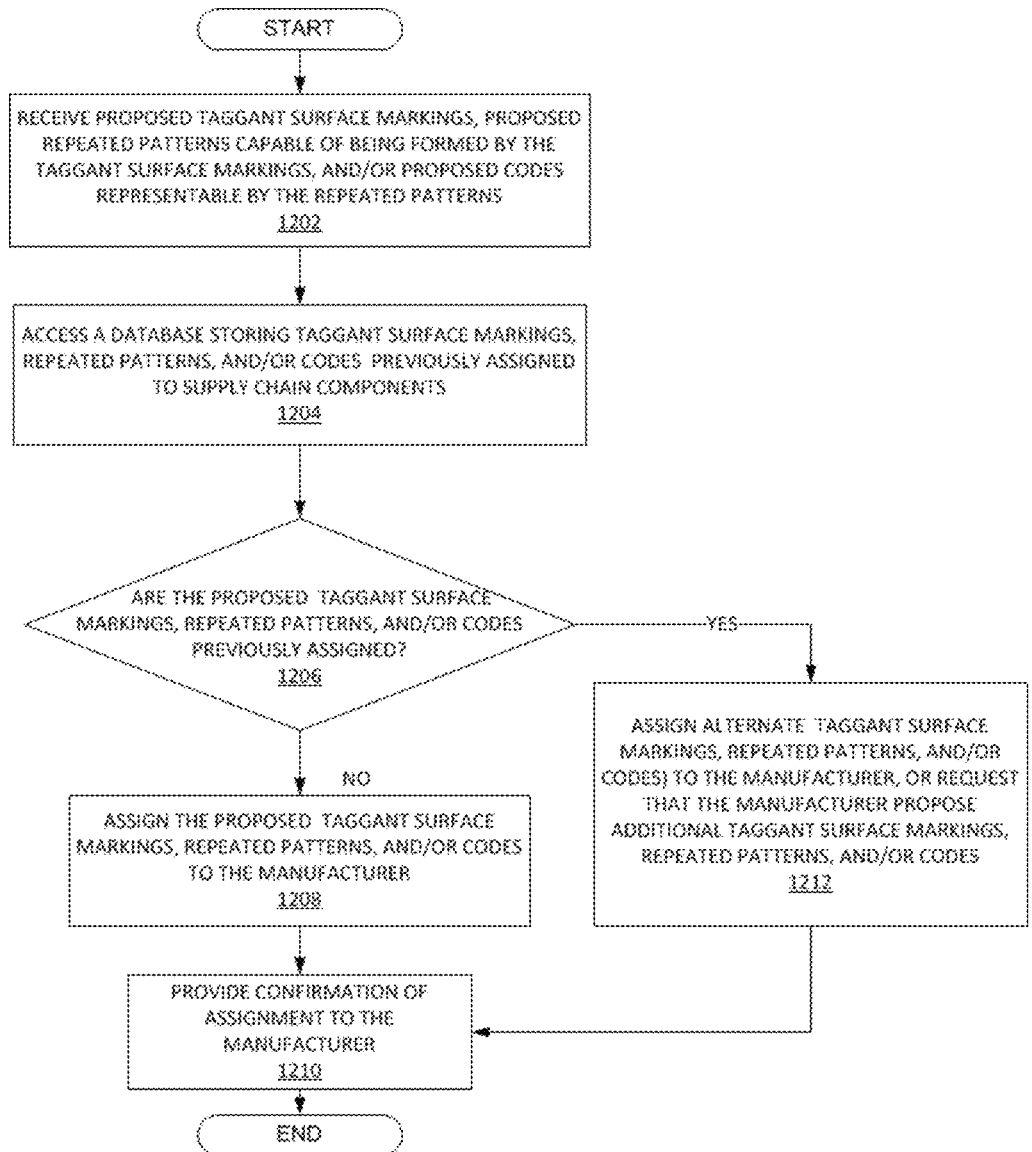
FIG. 12 illustrates a non-limiting example of a process for assigning taggant information to supply chain components, consistent with disclosed embodiments.

FIG. 12 illustrates a non-limiting example of a process for assigning, to supply chain components, taggant surface markings, repeated patterns, and code and code portions that uniquely represent the supply chain components, as seen and described above with respect to disclosed embodiments.

Listed below are non-limiting embodiments A1-A18.

A1. An acetate tow band comprising fibers, wherein the fibers comprise standard fibers and an identification fiber, wherein the standard fibers and identification fibers comprise cellulose acetate, wherein a ratio of a size of the identification fibers to a size of the standard fibers ($dpf_{ID\ fibers}:dpf_{STD\ fibers}$) is 1.5:1 or greater, wherein the identification fiber comprises one or more taggant surface markings, wherein the taggant surface markings form a repeated pattern along the length of the identification fiber, and wherein the taggant surface markings and the repeated pattern are representative of a bale identifier of the acetate tow band.

A2. The acetate tow band of embodiment A1, wherein the repeated pattern comprises an alphanumeric code, a digital code, an analog code, or an ideographic code.

A3. The acetate tow band of any of embodiments A1 or A2, wherein the repeated pattern includes metadata.

A4. The acetate tow band of embodiment A3, wherein the metadata comprises a read-start position, a read-end position, a read direction, spacing of the digits within the code.

A5. The acetate tow band of any of embodiments A1-A4, wherein the repeated pattern comprises a digital code and wherein the digital code comprises a binary code.

A6. The acetate tow band of embodiment A5, wherein a number of digits in the binary code ranges from 2 to 500, 4 to 100 10 to 100, 20 to 100, 4 to 50, 10 to 50, or 20 to 50.

A7. The acetate tow band of any of embodiments A1-A6, wherein a length of the repeated pattern ranges from 2 to 200 mm, 2 to 30 mm, 5 mm to 200 mm, 5 mm to 30 mm, 10 to 200 mm, or 10 to 30 mm.

A8. The acetate tow band of any of embodiments A1-A7, wherein the repeated pattern is essentially one-dimensional.

A9. The acetate tow band of any of embodiments A1-A8, wherein the repeated pattern is printed on the identification fibers.

A10. The acetate tow band of any of embodiments A1-A8, wherein the repeated pattern is engraved on the identification fibers.

A11. The acetate tow band of any of embodiments A2-A11, wherein the size of the standard fibers ranges from 1.0 dpf to 15.0 dpf; or wherein the size of the standard fibers ranges from 3.0 dpf to 15.0 dpf; or wherein the size of the standard fibers ranges from 3.0 dpf to 12.0 dpf; or wherein the size of the standard fibers ranges from 3.0 dpf to 10.0 dpf; or wherein the size of the standard fibers ranges from 4.0 dpf to 10.0 dpf.

A12. The acetate tow band of any of embodiments A1-A11, wherein the size of the identification fibers ranges from 3 dpf to 20 dpf; or wherein the size of the identification fibers ranges from 5 dpf to 20 dpf; or wherein the size of the identification fibers ranges from 8 dpf to 20 dpf; or wherein the size of the identification fibers ranges from 10 dpf to 20 dpf; or wherein the size of the identification fibers ranges from 12 dpf to 20 dpf; or wherein the size of the identification fibers ranges from 3 dpf to 15 dpf; or wherein the size of the identification fibers ranges from 5 dpf to 15 dpf; or wherein the size of the identification fibers ranges from 8 dpf to 15 dpf; or wherein the size of the identification fibers ranges from 15 dpf to 20 dpf.

A13. The acetate tow band of any of embodiments A1-A12, wherein the ratio of the size of the identification fibers to the size of the standard fibers ($dpf_{ID\ fibers}$:$dpf_{STD\ fibers}$) ranges from 1.5:1 to 10:1; or wherein the ratio of the size of the identification fibers to the size of the standard fibers ($dpf_{ID\ fibers}$:$dpf_{STD\ fibers}$) ranges from 1.5:1 to 5:1; or wherein the ratio of the size of the identification fibers to the size of the standard fibers ($dpf_{ID\ fibers}$:$dpf_{STD\ fibers}$) ranges from 1.5:1 to 3:1; or wherein the ratio of the size of the identification fibers to the size of the standard fibers ($dpf_{ID\ fibers}$:$dpf_{STD\ fibers}$) ranges from 1.5:1 to 2:1.

A14. The acetate tow band of any of embodiments A1-A13, wherein a total denier of the identification fibers ranges from 30 to 300 denier; or wherein the total denier of the identification fibers ranges from 30 to 200 denier; or wherein the total denier of the identification fibers ranges from 30 to 150 denier; or wherein the total denier of the identification fibers ranges from 50 to 100 denier.

A15. The acetate tow band of any of embodiments A1-A14, wherein the identification fibers are parallel to each other.

A16. The acetate tow band of any of embodiments A1-A17, wherein the identification fibers have a crenulated cross-section; or wherein one or more of the identification fibers have a cross-section shape distinct from the remaining identification fibers and the remaining identification fibers have a crenulated cross-section.

A17. A filter rod comprising any of the acetate tow bands of embodiments A1-A16.

A18. A cigarette filter comprising any of the acetate tow bands of embodiments A1-A16.

Listed below are non-limiting embodiments B1-B7.

B1. A method of making an acetate tow band comprising fibers, wherein the fibers comprise standard fibers and identification fibers, wherein the standard fibers and identification fibers comprise cellulose acetate, wherein the method comprises: (a) obtaining the identification fibers (b) producing the standard fibers on a first fiber production process; and (c) combining the identification fibers and the standard fibers into the acetate tow band, wherein a ratio of a size of the identification fibers to a size of the standard fibers ($dpf_{ID\ fibers}$:$dpf_{STD\ fibers}$) is 1.5:1 or greater, wherein the identification fibers comprise one or more taggant surface markings, wherein the taggant surface markings form a repeated pattern along a length of the identification fibers, and wherein the taggant surface markings and the repeated pattern are representative of a bale identifier of the acetate tow band.

B2. The method of embodiment B1, wherein the obtaining of the identification fibers comprises at least one of (i) producing the portion of the identification fibers on the second fiber production process followed by applying the taggant surface markings in the repeated pattern to the identification fibers; (ii) receiving the portion of the identification fibers from a third party followed by applying the taggant surface markings in the repeated pattern to the identification fibers; or (ii) receiving a portion of the identification fibers having the taggant surface markings in the repeated pattern from the third party.

B3. The method of embodiment B2, wherein applying the taggant surface markings in the repeated pattern comprises engraving, printing, or morphological modification; or wherein applying the taggant surface markings in the repeated pattern comprises engraving; or wherein applying the taggant surface markings in the repeated pattern comprises printing.

B4. The method of embodiment B3, wherein the applying comprises printing the taggant surface markings in the repeated pattern on the identification fibers concurrently to producing the standard fibers and combining the identification fibers and the standard fibers before crimping the acetate tow band.

B5. The method of embodiment B3, wherein the applying comprises laser engraving the taggant surface markings in the repeated pattern on the identification fibers concurrently to producing the standard fibers and combining the identification fibers and the standard fibers before crimping the acetate tow band.

B6. The method of any of embodiments B2-B5, wherein the first fiber production process comprises the second fiber production process.

B7. The method of any of embodiments B1-B6, producing any of the acetate tow bands of embodiments A2-A16.

Listed below are non-limiting embodiments C1-C5.

C1. A method of characterizing a cigarette filter, wherein the cigarette filter comprises an acetate tow band, wherein the acetate tow band comprises fibers, wherein the fibers comprise standard fibers and identification fibers, wherein the fibers comprise cellulose acetate, wherein a ratio of a size of the identification fibers to a size of the standard fibers ($dpf_{ID\ fibers}$:$dpf_{STD\ fibers}$) is 1.5:1 or greater, wherein the taggant surface markings form a repeated pattern along a length of the identification fibers, and wherein the method comprises (a) locating the identification fibers by exploiting the ratio of the size of the identification fibers to the size of the standard fibers; (b) separating the identification fibers from the cigarette filter; (c) applying imaging technology to at least one of the identification fibers; (d) detecting the taggant surface markings; (e) determining at least a portion of the repeated pattern of the taggant surface markings, wherein the taggant surface markings and the repeated pattern are representative of at least one supply chain component of the acetate tow band; and (f) generating, based on the detection and determination, supply chain information correlating the taggant surface markings and the repeated pattern to at least one supply chain component of the acetate tow band.

C2. The method of embodiment C1, wherein the separating comprises physically segregating the identification fibers from the rest of the cigarette filter.

C3. The method of any of embodiments C1 or C2, wherein the imaging technology is selected from the group consisting of visual inspection, magnification, microscopy, electron microscopy, confocal microscopy, and optical scanning; or wherein the imaging technology is selected from the group consisting of magnification, microscopy, electron microscopy, confocal microscopy, and optical scanning.

C4. The method of any of embodiments C1-C3, wherein the at least one supply chain component comprises the manufacturer of the acetate tow band; or wherein the at least one supply chain component comprises the bale identifier of the acetate tow band.

C5. The method of any of embodiments C1-C4, wherein the cigarette filter comprises any of the acetate tow bands of embodiments A2-A16.

EXAMPLES

Example 1—Feasibility of Laser Engraving 20 Dpf Cellulose Acetate Fibers

A set of 20 dpf cellulose acetate fibers with crenulated cross-section where spun from a single spinneret containing 10 round holes and wound onto a spool. The lubricant used was fit-for-use in an acetate tow manufactured for cigarette filters. The filaments were not twisted or entangled, but simply wound onto the spool with the filaments essentially parallel to one another.

Figure 2:
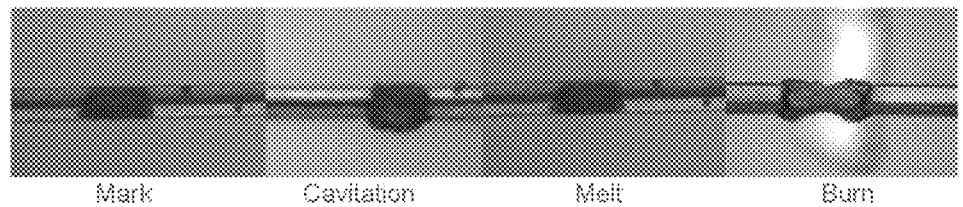
FIG. 2 shows a photomicrograph of a cellulose acetate fiber with laser engravings applied for different intensities.

The 10 filaments of 20 dpf cellulose acetate fibers where positioned for applying surface markings using a MACSA K-1000 series $CO_2$ laser. The fibers remained stationary as the laser moved across the fibers at a speed of 60,000 millimeters/second. The laser intensity (percent power) was varied as shown in Table 1 and the surface markings were observed. At lower intensities, the cellulose acetate filament displayed a darkened spot or mark. As exposure to the laser intensified, the surface underwent cavitation and material created a raised area. This raised area then collapsed back into the fiber resulting in a surface marking indistinguishable from that produced by lower laser intensities. Finally, at higher laser intensity, the fiber continued to melt until it burned through. See FIG. 2 for examples of each stage of exposure. Note the degree of marking is also a function of the time the fiber is exposed to the laser (see Example 2).

The results are given in Table 1. Result descriptions correspond to no visible markings (no marks), partial or inconsistent markings (marked sometimes), quality markings corresponding to "mark" or "melt" images in FIG. 2 (good mark), or melting of the fiber sufficient to cause the fiber to break (burned in two).

TABLE 1

Observations of marking on 20 dpf cellulose acetate fibers laser engraved at laser speed of 60K mm/s at different laser intensities

| Power (%) | Results |
|---|---|
| 15 | No marks |
| 18 | No marks |
| 21 | Marked sometimes |
| 24 | Marked sometimes |
| 51 | Good marks |
| 54 | Good marks |
| 57 | Good marks |
| 60 | Starting to burn |
| 70 | Starting to burn |
| 80 | Burned in two |
| 90 | Burned in two |
| 100 | Burned in two |

Example 2—Feasibility of Laser Engraving 15 Dpf Cellulose Acetate Fibers

Example 1 was repeated except that 10 filaments of 15 dpf cellulose acetate fibers were used and surface marked at the percent power and laser speed as given in Table 2. Observations are also given in Table 2.

TABLE 2

Observations of marking on 15 dpf cellulose acetate fibers laser engraved at different laser intensities and laser speeds

| Power (%) | Speed (mm/s) | Results |
|---|---|---|
| 5 | 30k | No marks |
| 10 | 30k | No marks |
| 20 | 30k | Marked sometimes |
| 30 | 30k | Good marks |
| 40 | 30k | Burned in two |
| 5 | 60k | No marks |
| 10 | 60k | No marks |
| 50 | 60k | Good marks |

Example 2 and Example 3 showed the feasibility of applying surface markings to cellulose acetate fibers via laser engraving. Initial attempts to use the MACSA K-1000 series $CO_2$ laser to laser engrave 19 filaments of 8 dpf cellulose acetate fibers and 13 filaments of 12 dpf cellulose acetate fibers were unsuccessful due to the laser burning the fibers in two.

Example 3—Laser Engraving Moving Cellulose Acetate Fibers

Figure 3:
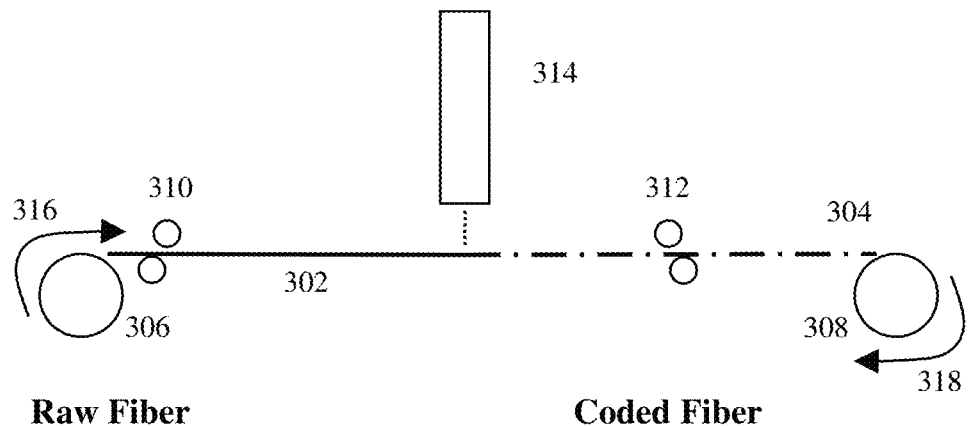
FIG. 3 illustrates a schematic of the process set up for Examples 2 and 3.

In order to produce acetate tow fibers with surface markings along sufficient length to incorporate into an acetate tow band and produce filter rods, a simply system was set up to remove fibers from a first spool, mark the fibers, and wind the marked fibers onto a second spool. The experimental system as depicted in FIG. 3 was set up to apply surface markings to the fibers using MACSA K-1000 series $CO_2$ laser 314. 10 filaments of 20 dpf cellulose acetate fibers 302 were unwound in clockwise direction 316 from spool 306 while being guided by guide rolls 310. Unmarked cellulose ester fibers 302 were laser engraved as they traveled below laser 314. Marked cellulose acetate fibers 304 were guided by guide rolls 312 and wound in a clockwise direction 318 unto spool 308. Spool 308 was wound such that the linear speed of the fibers remained constant. The percent power (intensity of the laser) was set at 55% and the laser speed was set a 60 k mm/s.

Figure 4A:
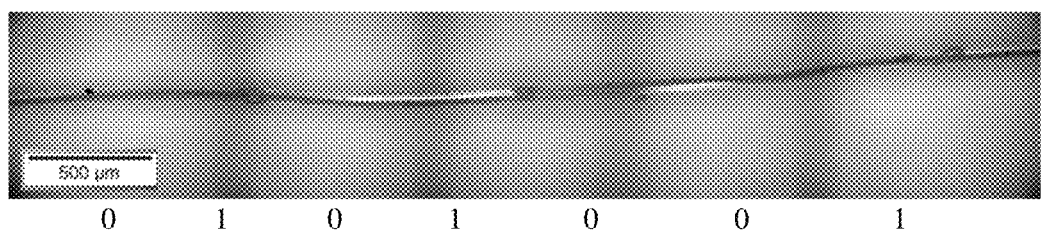
FIGS. 4(a) and 4(b) show the code on a 20 dpf cellulose acetate fiber of Example 3.
Figure 4B:
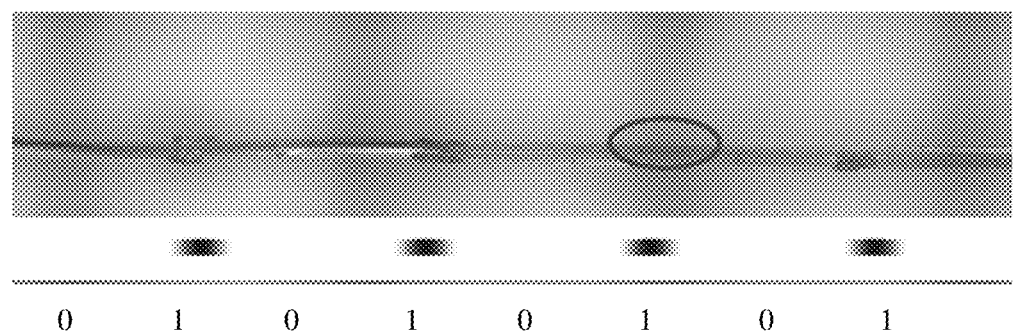

FIGS. 4(a) and 4(b) are pictures of two sections of fiber analyzed. FIG. 4(a) shows a section of code that was completely and accurately surface marked on the fiber. FIG. 4(b) shows a section of code with one of the surface markings missing. Defects such as that shown in FIG. 4(b) were related to the need to ensure better speed control, fiber placement relative to the laser, and minimal vibration of fibers as they are being marked.

Example 4—Adding Surface Marked Fiber to Tow and Making Filter Rods

Spool 308 (FIG. 3) of encoded 20 dpf cellulose acetate fibers was withdrawn from its package and fed into the tow band of a cellulose acetate tow production process prior to the crimper. The cellulose acetate tow was a typical commercial, "Y" cross section tow item with a nominal 3.5 filament denier and 30,000 total denier. The tow with the encoded cellulose acetate fibers was crimped, conditioned and delivered to a baler using standard manufacturing conditions.

Filter rods were produced from the tow on an AF2N plug maker at a tape speed of 300 m/m, forming a filter rod of 120 mm in length of typical tow weights and Triacetin plasticizer levels used in the tobacco industry. After a delay of sufficient time for the plasticizer to cure, or harden in the filter, the encoded fiber was manually extracted from rods and inspected with a microscope. There were no observable changes to the surface markings of the cellulose fibers after applying the laser markings as compared to after extracting the surface-marked fibers from the filter rod.

Example 5—Adding Surface Marked Fiber to Tow and Making Filter Rods

Example 4 was repeated except that the surface-marked fibers were added to a cellulose acetate tow with a nominal 4.5 denier per filament and a 30,000 total denier. Again, there were no observable changes to the surface markings of the cellulose fibers after applying the laser markings as compared to after extracting the surface-marked fibers from the filter rod.

Other embodiments will be apparent to those skilled in the art from consideration of the specification and practice of the embodiments disclosed herein. It will be understood that variations and modifications can be effected within the spirit and scope of the disclosed embodiments. It is further intended that the specification and examples be considered as exemplary only, with a true scope and spirit of the disclosed embodiments being indicated by the following claims.

We claim:

1. An acetate tow band comprising fibers, wherein the fibers comprise standard fibers and identification fibers, wherein the standard fibers and the identification fibers comprise cellulose acetate, wherein a ratio of a size of the identification fibers to a size of the standard fibers ($dpf_{ID\ fibers}$:$dpf_{STD\ fibers}$) is 1.5:1 or greater,
wherein the identification fibers comprise one or more taggant surface markings,
wherein the taggant surface markings form a repeated pattern along a length of the identification fibers, and
wherein the taggant surface markings and the repeated pattern are representative of a bale identifier of the acetate tow band.

2. The acetate tow band of claim 1, wherein the repeated pattern comprises an alphanumeric code, a digital code, an analog code, or an ideographic code.

3. The acetate tow band of claim 2, wherein the repeated pattern comprises metadata and wherein the metadata comprises a read-start position, a read-end position, a read direction, and/or spacing of digits within the code.

4. The acetate tow band of claim 2 wherein the repeated pattern comprises the digital code, wherein the digital code comprises a binary code, and wherein a number of digits in the binary code ranges from 4 to 100.

5. The acetate tow band of claim 1, wherein the repeated pattern is engraved on the identification fibers.

6. The acetate tow band of claim 1, wherein the repeated pattern is printed on the identification fibers.

7. The acetate tow band of claim 1, wherein the size of the standard fibers ranges from 1.0 dpf to 15.0 dpf.

8. The acetate tow band of claim 1, wherein the ratio of the size of the identification fibers to the size of the standard fibers ($dpf_{ID\ fibers}$:$dpf_{STD\ fibers}$) ranges from 1.5:1 to 10:1.

9. The acetate tow band of claim 1, wherein a total denier of the identification fibers ranges from 30 to 300 denier.

10. The acetate tow band claim 1, wherein the identification fibers are parallel to each other.

11. The acetate tow band of claim 1, wherein the identification fibers have a crenulated cross-section.

12. A method of producing an acetate tow band comprising fibers, wherein the fibers comprise standard fibers and identification fibers, wherein the standard fibers and identification fibers comprise cellulose acetate, wherein the method comprises:
(a) obtaining the identification fibers;
(b) producing the standard fibers on a first fiber production process; and
(c) combining the identification fibers and the standard fibers into the acetate tow band,
wherein a ratio of a size of the identification fibers to a size of the standard fibers ($dpf_{ID\ fibers}$:$dpf_{STD\ fibers}$) is 1.5:1 or greater,
wherein the identification fibers comprise one or more taggant surface markings, wherein the taggant surface markings form a repeated pattern along a length of the identification fibers, and
wherein the taggant surface markings and the repeated pattern are representative of a bale identifier of the acetate tow band.

13. The method of claim 12, wherein the obtaining of the identification fibers comprises at least one of
(i) producing of a portion of the identification fibers on a second fiber production process followed by applying the taggant surface markings in the repeated pattern to the identification fibers;
(ii) receiving a portion of the identification fibers from a third party followed by applying the taggant surface markings in the repeated pattern to the identification fibers; or (ii) receiving a portion of the identification fibers having the taggant surface markings in the repeated pattern from the third party.

14. The method of claim 13, wherein applying the taggant surface markings in the repeated pattern comprises engraving.

15. The method of claim 13, wherein applying the taggant surface markings in the repeated pattern comprises printing.

16. The method of claim 12, wherein the repeated pattern comprises a digital code, wherein the digital code comprises a binary code, and wherein a number of digits in the binary code ranges from 4 to 100.

17. A method of characterizing a cigarette filter, wherein the cigarette filter comprises an acetate tow band,
wherein the acetate tow band comprises fibers,
the fibers comprise standard fibers and identification fibers,
the standard fibers and the identification fibers comprise cellulose acetate,
wherein a ratio of a size of the identification fibers to a size of the standard fibers ($dpf_{ID\ fibers}:dpf_{STD\ fibers}$) is 1.5:1 or greater,
wherein the identification fibers exhibit one or more taggant surface markings,
wherein the taggant surface markings form a repeated pattern along a length of the identification fibers, and
wherein the method comprises
  (a) locating the identification fibers by exploiting the ratio of the size of the identification fibers to the size of the standard fibers;
  (b) separating the identification fibers from the cigarette filter;
  (c) applying imaging technology to at least one of the identification fibers;
  (d) detecting the taggant surface markings;
  (e) determining the repeated pattern of the taggant surface markings,
  wherein the taggant surface markings and the repeated pattern are representative of at least one supply chain component of the acetate tow band; and
  (f) generating, based on the detection and determination, supply chain information correlating the taggant surface markings and the repeated pattern to at least one supply chain component of the acetate tow band.

18. The method of claim 17, wherein the separating comprises physically segregating the identification fibers from the cigarette filter.

19. The method of claim 17, wherein the imaging technology is selected from the group consisting of visual inspection, magnification, microscopy, electron microscopy, confocal microscopy, and optical scanning.

20. The method of claim 17, wherein the at least one supply chain component comprises a manufacturer of the acetate tow band and/or a bale identifier of the acetate tow band.

* * * * *